(12) United States Patent
Mordekhay

(10) Patent No.: US 6,825,466 B2
(45) Date of Patent: Nov. 30, 2004

(54) APPARATUS AND METHOD FOR AUTOMATED SAMPLE ANALYSIS BY ATMOSPHERIC PRESSURE MATRIX ASSISTED LASER DESORPTION IONIZATION MASS SPECTROMETRY

(75) Inventor: Vladimir Mordekhay, Campbell, CA (US)

(73) Assignee: Automated Biotechnology, Inc., Menlo Park, CA (US)

( * ) Notice: Subject to any disclaimer, the term of this patent is extended or adjusted under 35 U.S.C. 154(b) by 0 days.

(21) Appl. No.: 10/615,733

(22) Filed: Jul. 9, 2003

(65) Prior Publication Data

US 2004/0021071 A1 Feb. 5, 2004

Related U.S. Application Data

(60) Provisional application No. 60/400,006, filed on Aug. 1, 2002.

(51) Int. Cl.$^7$ ................................................ H01J 49/04
(52) U.S. Cl. ........................ 250/288; 250/281; 250/282; 250/289; 250/442.11; 250/440.11; 250/441.11
(58) Field of Search ................................. 250/288, 281, 250/282, 289, 442.11, 440.11, 441.11

(56) References Cited

U.S. PATENT DOCUMENTS

| | | | |
|---|---|---|---|
| 5,288,644 A | | 2/1994 | Beavis et al. |
| 5,498,545 A | * | 3/1996 | Vestal ........................... 436/47 |
| 5,965,884 A | * | 10/1999 | Laiko et al. ................. 250/288 |
| RE37,485 E | | 12/2001 | Vestal |
| 6,541,768 B2 | | 4/2003 | Andrien, Jr. et al. |

OTHER PUBLICATIONS

Agilent Technologies Inc., Sample Handling Interface for AP–MALDI (see http://www.apmaldi.com/Products.Htm).

* cited by examiner

Primary Examiner—Nikita Wells

(57) ABSTRACT

The apparatus of the invention consists of two module, one of which carries an sample plate handling device, which is docked to the mass spectrometer in a working position for loading ionized samples from the atmospheric pressure environment to the vacuum chamber of the mass spectrometer, while the other one is used for picking up the sample plate carrier with preliminarily prepared and inserted sample plates into and from the storage cassette and for transferring the sample plates carriers to a stand-by position. The sample plate handling device is moveable between the aforementioned working position and the stand-by position and is provided with means for taking the stand-by sample plate from the carrier and for holding it during delivery of the ionized samples to the mass spectrometry, as well as with means for shifting the sample plate inside the sample plate handling device in the X-Y coordinate system for arranging a selected sample cell coaxially with the center of the ion-sampling orifice. The first module provides movements in the Z-axis and X-axis directions, and the second module provides movements in the Z-axis and Y-axis direction. As the mechanisms of the aforementioned modules operate under atmospheric pressure, they do not need the use of any special and expensive sealing devices required for use of similar mechanisms in vacuum. The system is fully automated and movements of all mechanisms and drives are controlled by a data preliminarily inputted to a central processing unit provided in the control system of the apparatus. The apparatuses of the second and third embodiments have only one module in conjunction with the combined target flange that also functions as a mechanical arm of a robot.

39 Claims, 12 Drawing Sheets

APPARATUS AND METHOD FOR AUTOMATED SAMPLE ANALYSIS BY ATMOSPHERIC PRESSURE MATRIX ASSISTED LASER DESORPTION IONIZATION MASS SPECTROMETRY

CROSS-REFERENCE TO RELATED APPLICATIONS

The subject matter of this patent application claims the benefit of U.S. Provisional Patent Application No. 60/400,006 filed on Aug. 1, 2002 the full disclosure of which is incorporated herein by reference.

FIELD OF THE INVENTION

The present invention relates to the field of chemistry and biochemistry and, in particular, to the analytical methods and apparatuses for loading, unloading and analyzing samples by atmospheric pressure matrix assisted laser desorption ionization (AP-MALDI) technique.

PRIOR ART AND DISADVANTAGE OF THE PRIOR ART

Mass spectrometers have become one of the essential tools of the biochemistry lab. Biochemists take advantage of the capabilities of mass spectrometers to determine molecular weights of biomolecules, monitor bioreactions, detect post-translational modifications, perform protein, and oligo-nucleotide sequencing, and many more applications. During the past decade, one of the methods, which became most successful for the mass spectrometric analysis and investigation of large molecules is a method known as MALDI (Matrix-Assisted Laser Desorption Ionization). This method, which in application to time-of-flight (TOF) mass spectrometry (MS) is known as MALDI-TOF MS, is a relatively novel technique in which a co-precipitate of an UV-light absorbing matrix and a biomolecule is irradiated by a nanosecond laser pulse. The sample (analyte) is suspended or dissolved in a matrix (e.g., in 1000× molar excess).

Most of the laser energy is absorbed by the matrix, which prevents unwanted fragmentation of the biomolecule. Matrices are small organic compounds that are co-crystallized with the analyte. It seems that the presence of the matrix, spares the analyte from degradation, resulting in the detection of intact molecules as large as 1 million Da. The ionized biomolecules are accelerated in an electric field and enter the flight tube. During the flight in this tube, different molecules are separated according to their mass to charge ratio and reach the detector at different times. In this way each molecule yields a distinct signal. The method is used for detection and characterization of biomolecules, such as proteins, peptides, oligosaccharides and oligonucleotides, with molecular masses between 400 and 350,000 Da. It is a very sensitive method, which allows the detection of low ($10^{-15}$ to $10^{-18}$ mole) quantities of sample with a mass accuracy of 0.1–0.01% or higher.

Another advantage of MALDI is that this method allows for vaporization and ionization of non-volatile biological samples from a solid-state phase directly into the gas phase.

The most important step in MALDI, is sample preparation. During this step, the matrix and analyte are mixed and the mixture is dried on a probe or as it is more common now, on a sample plate. Upon preparation, the sample plate with samples is loaded into the mass spectrometer.

A laser beam, serves as the desorption and ionization source in MALDI. The matrix plays a key role in this technique by absorbing the laser light energy and causing part of the illuminated substrate to vaporize. A rapidly expanding matrix plume carries some of the analyte into the vacuum with it and aids the sample ionization process. The matrix molecules absorb most of the incident laser energy minimizing sample damage and ion fragmentation (i.e., soft ionization). Nitrogen lasers operating at 337 nm (a wavelength that is well absorbed by most UV matrices) are the most common illumination sources because they are inexpensive and offer the ideal combination of power/wavelength/pulsewidth. However, other UV and even IR pulsed lasers have been used with properly selected matrices.

Once the sample molecules are vaporized and ionized, they are transferred, e.g., into a time-of-flight mass spectrometer (TOF-MS) where they are separated from the matrix ions, and individually detected, based on their mass-to-charge (m/z) ratios and analyzed. High transmission and sensitivity, along with theoretically unlimited mass range are among the inherent advantages of TOF instruments. Detection of the ions at the end of the tube is based on their flight time, which is proportional to the square root of their m/z.

Roughly, the MALDI system can be divided into two groups: VP-MALDI for matrix-assisted laser desorption at vacuum pressure and AP-MALDI for matrix-assisted laser desorption at atmospheric pressure. A characteristic feature of vacuum-pressure ionization sources is that sample ionization occurs inside a mass spectrometer housing under vacuum conditions. In contrast to vacuum ionization, any atmospheric pressure ionization takes place outside a mass spectrometer instrument. It should be noted that different instrument types are used in both cases. However, for sampling atmospheric pressure ions any mass spectrometer must be equipped with Atmospheric Pressure Interface (API) to transfer ions from an external region of atmospheric pressure to a mass analyzer under high vacuum.

Examples of both these systems are given below for more detailed familiarization with the MALDI technique.

U.S. Pat. No. 5,288,644 issued in Feb. 22, 1994 to Ronald C. Beavis, et al. discloses an apparatus and method for the sequencing of genome. The apparatus comprises an automated DNA sampler, which adds a matrix solution from a container to separated DNA samples. A large number of DNA fragment samples, for example 120 samples, may be loaded into a sample tray. The matrix solution may be added automatically to each sample using procedures available on the aforementioned autosampler, and the samples may then be spotted sequentially as sample spots on an appropriate surface, such as the planar surface of the disk rotated by a stepper motor. Sample spot identification is entered into the data storage and computing system, which controls both the autosampler and the mass spectrometer. The location of each spot relative to a reference mark is recorded in the computer. Sample preparation and loading onto the solid surface is done off-line from the mass spectrometer, and multiple stations may be employed for each mass spectrometer, if the time required for sample preparation is longer than the measurement time.

Once the samples in suitable matrix are deposited on the disk, the disk may be inserted into the ion source of a mass spectrometer through the vacuum lock. Any gas introduced in this procedure must be removed prior to measuring the mass spectrum. Loading and pump down of the spectrometer typically requires two to three minutes, and the total time for measurement of each sample to obtain a spectrum is typically one minute or less.

Thus, the above-described VP-MALDI technique requires that the sample plate carrier be loaded into the mass spectrometer through a vacuum lock and even though manipulations with the sample support are carried out automatically and coordinated by the computer, all sampler operations for loading the samples into the mass spectrometer are performed in vacuum. Such a system requires the use of complicated vacuum seals and special drive, transportation, and actuation mechanisms, which have to be vacuum-proof. Furthermore, the sample loading system of U.S. Pat. No. 5,288,644 has a relatively low throughput rate. As the authors of the above invention states, the system is limited to about 50 complete DNA spectra per hour. Furthermore, the system is expensive, as it requires the use of vacuum-proof sample plate carrier handling mechanisms.

U.S. Reissued Patent RE 37,485 filed by Marvin L. Vestal and published on Dec. 25, 2001 describes another mass spectrometer system and method for vacuum-pressure matrix-assisted laser desorption measurements. The system is equipped with a sample plate transport mechanism for automatically inputting and outputting each of the sample plates into and from the sample-receiving chamber of the mass spectrometer.

A sample support or plate used in the aforementioned system comprises a thin, substantially square plate of stainless steel or other suitable electrically conducting material approximately 1.5 mm thick and 50 mm wide. The plate may contain precisely located holes to allow the position and orientation of the plate to be accurately determined relative to a moveable stage, which is required both in the sample loading step and in the ion source of the mass spectrometer. The sample plate also contains a plurality of precisely determinable sample positions on the upper sample-receiving surface of the plate. The sample plate may thus contain 100 sample positions each identified by a sample spot, which is about 2.5 mm in diameter in a precisely known location on the plate, with each sample support being suitable for accepting a few microliters of sample solution.

The sample plate is rigidly attached to a ferromagnetic material handle, which is used to engage an electromagnetic device for the purpose of transporting the sample plate between component systems. The sample plate has two or more precisely located holes which locate the sample plate carrier when installed in the sample receiving stage in the ion source of the mass spectrometer and in the sample transport trays.

Processing and preparing samples may be different, depending on the application, the types of samples to be tested, and the degree to which the samples are prepared and purified prior to being input to the analysis system.

The sample processing components include an autosampler, valves for controllably adding an appropriate solution of matrix from containers to each sample, and a pump or another flow system for transferring liquid samples from a selected sample to a known sample position on the sample plate. The sample plate is precisely located on a carrier mounted on a computer-controlled x-y table. Each sample position may be computer recorded at the time the sample aliquot is transferred to the plate. The autosampler may be similar to autosamplers used with capillary electrophoresis. The above-described sample input and preparation operations are carried out under atmospheric pressure prior to loading to the vacuum chamber of the mass spectrometer.

When each sample location on a plate has been loaded with a sample, the samples are allowed to dry before the plate is transferred into the vacuum chamber of the mass spectrometer. In the simplest case, the plates may be transferred from the sample loading system to a rack or cassette where they are allowed to dry in laboratory air, and preferably in a sealed chamber equipped with a computer-controlled door which allows the samples to be dried in an environment in which the pressure, temperature, and composition of the surrounding atmosphere is controlled. In the fully automated mode, each of the loaded and dried sample plates may be transferred from the sample plate storage chamber or cassette to an adjacent mass spectrometer.

The manual step involved in loading the sample plates may be eliminated by adding to the vacuum lock chamber of a mass spectrometer a sample storage region. This provision, when coupled with on-line sample loading, allows the system to be operated in a fully automatic, unattended mode. In this configuration, an input door is located between the vacuum lock chamber and the storage chamber. An air cylinder transporter equipped with electromagnets is provided for transporting sample plates from the transport tray within the storage chamber to the vacuum lock chamber. The tray contains multiple shelves and corresponding slots each for storing a sample plate. A cassette transport device mechanism including a lead screw driven by a stepper motor is provided to allow any selected one of these slots and a corresponding plate in the cassette to be brought into line with transporter.

The above-described loading system allows the sample plates to be loaded into the storage region of the vacuum lock chamber, while another sample plate is being analyzed in the ion source chamber of a mass spectrometer. In fully automatic operation, whenever a new sample plate may be loaded, the storage chamber is evacuated, the input door between the storage chamber and the vacuum lock chamber is opened, and the new sample plate is automatically moved by transporter to a sample transport tray provided in the vacuum lock chamber. The input door is then closed and the vacuum lock chamber remains evacuated. The plate positioned by the sample transport tray is moved within chamber by an air cylinder transport mechanism.

When analysis of the samples on one plate within the ion source is completed, the plate is ejected and placed in a vacant slot in the sample storage cassette. This cassette is then moved by a stepper motor and a lead screw to bring a new sample plate in the transport tray.

Thus, as has been shown above, the VP-MALDI system of U.S. RE 37,485 is characterized by the use of a plurality of sample supports which are transferable between the sample preparation station and the mass spectrometer with the use of a x-y transport mechanism so that when one of the sample supports is located inside the vacuum chamber of the mass spectrometer, other sample supports are loaded with the samples and prepared for the analysis. However, the transfer from the preparation station to the vacuum chamber and in the opposite direction is always carried out through the vacuum lock. This intermediate transfer operations delays the throughput of the system as a whole since before loading a sample plate into the storage chamber for subsequent analysis by the mass spectrometer, the sample loading doors of the vacuum lock should be closed, the pumpout valve should be connected to the mechanical vacuum pump, the latter should be open, the sample storage chamber should be evacuated to a predetermined acceptable vacuum level (e.g., 20 millitorr), input and output doors should be opened and allow sample plates to be transported between the sample storage chamber and the ion source chamber of the mass spectrometer without significantly degrading the vacuum of the mass spectrometer. Execution of these sequential operations requires time and therefore, in spite of a provision of fully automated loading/unloading mechanisms, the VP-MALDI system has some limitations with regard to the system throughput. Furthermore, a provision of the sample storage chamber with an appropriate valve system for evacuation of this chamber makes the structure of the system more complicated and expensive.

Another disadvantage of the sample plate delivery system of the aforementioned reissued patent is that two different mechanisms are required for picking up and delivery of the sample plates to the location from where the samples are introduced into the mass spectrometer (in the above case, to the vacuum lock) and for retaining the sample plate in the aforementioned location.

A serious disadvantage of the aforementioned system is that for picking up sample plates the handling mechanisms come in direct contact with each sample plate, and this increases a chance of contamination of the samples and of the sample plates themselves.

Another serious disadvantage of the automatic loading/unloading systems for VP-MALDI is that the mechanisms for operation in vacuum must be provided with reliable vacuum seals and therefore such mechanisms are complicated in structure and very expensive to manufacture. They also are expensive and complicated in maintenance.

In order to eliminated disadvantages of the vacuum-pressure MALDI, an atmospheric-pressure MALDI (hereinafter referred to as AP-MALDI) system was developed. At the present time, the AP-MALDI has become a technique that competes in sensitivity and selectivity with conventional VP-MALDI. In the AP-MALDI, the samples deposited on sample plates do not need to be delivered into the vacuum chamber, and only the plum of ions produced by laser radiation is sampled into an atmospheric pressure ionization mass spectrometer.

An example of a AP-MALDI system is the one disclosed in U.S. Pat. No. 5,965,884 issued on Oct. 12, 1999 to Victor V. Laiko, et al. This AP-MALDI apparatus comprises an ionization chamber, an interface for connecting the ionization chamber to a spectrometer, a sample plate or support with sample deposited on its target surface, a laser, and a lens for focusing a laser beam generated by the laser.

The ionization chamber is used to contain a bath gas or gas mixture, which is at atmospheric pressure or near atmospheric pressure. Dry nitrogen and dry air is normally used as the bath gas. A gas inlet is incorporated in the gas chamber, which provides the pathway for the bath gas to enter the ionization chamber. The ionization chamber also has a window for the laser beam to enter the chamber. Additional equipment can be incorporated into the ionization chamber to further control the humidity, the temperature and the pressure of the bath gas.

The interface, which is usually a part of the spectrometer, comprises an inlet orifice, through which ionized analyte particles enter the spectrometer from the ionization chamber. The inlet orifice is connected to a electric power supply to serve as an electrode.

The sample support is also connected to an electric power supply, which also serves as an electrode. The two electrodes of the inlet orifice and the sample support provide the electric field which helps move the ionized analyte from the sample support to the inlet orifice. The electric potential applied to the electrodes is adjusted to optimize the signal level measured by the spectrometer.

The sample is deposited on a target surface of the sample support, which is aligned with the inlet orifice of the interface to facilitate the ionized analyte to move to the inlet orifice.

The laser positioned outside the ionization chamber is a UV laser, a visible laser, or an IR laser. The laser beam is focused by a lens. The position of the lens is adjusted so that best measurement results are achieved by the spectrometer.

The AP-MALDI has the following advantages as compared to the VP-MALDI. The AP-MALDI takes place under atmospheric pressure conditions. This allows a more or less uniform ion cloud to form after laser illumination, because the produced ions achieve a thermal equilibrium with the surrounding bath gas molecules quickly through collision. As a consequence, the AP-MALDI technique produces a quasi-continuous ion source, which provides a stable ion supply to a mass spectrometer.

A more powerful laser pulse can be used in AP-MALDI because vibrationally excited analyte ions are quickly thermalized (stabilized) with the surrounding bath gas molecules before they dissociate into fragments. Furthermore, a larger laser spot is used to illuminate the sample, which allows an easier alignment procedure in comparison with the vacuum MALDI technique. As a consequence, substantial amount of ions, as much as a few picomoles, are generated in AP-MALDI to compensate for the loss due to API.

AP-MALDI has an ion source, which is external with respect to the spectrometer instrument. Thus any mass spectrometer equipped with Atmospheric Pressure Interface (API) may be easily coupled with this ion source without undue effort. The de-coupling of ion source from the ion-focusing optics of a spectrometer ensures the same resolution level and spectra calibration procedure as for any other atmospheric pressure ionization technique. As a result, different mass analyzers, such as quadrupole ion-trap type, time-of-flight type, and Fourier transform ion cyclotrone resonance type or mass analyzers of other types may be easily coupled with AP-MALDI.

Atmospheric pressure character of AP-MALDI allows a simple sample loading procedure. Consequently, the construction of the instrument is simplified drastically. Both sample preparation and ionization processes take place under atmospheric pressure conditions.

AP-MALDI is a versatile technique. The selection of possible matrix material for AP-MALDI is not limited to solids or liquid matrixes with very low vapor pressures. The most important feature of the AP-MALDI as compared to the VP-MALDI is that matrixes of volatile liquids may be used only under atmospheric pressure conditions without the use of any special procedures and devices.

However, a disadvantage of the atmospheric-pressure system of U.S. Pat. No. 5,965,884 is that it is associated with manual loading/unloading procedures of the sample supports.

U.S. Pat. No. 6,541,768 issued on Apr. 1, 2003 to Bruce A. Andrien, Jr., et al. discloses a multiple sample introduction system for API (atmospheric pressure ionization) mass spectrometry. In this system, the electrospray ion source is interfaced to a mass spectrometer, which is configured in vacuum chamber. Individual electrospray (ES) probe assemblies can be configured in the electrospray ion source atmospheric pressure chamber, where solution is sprayed from individual probe tips. In one of the embodiments, the electrospray source is configured with an ES probe assembly comprised of six ES tips with individual liquid supply lines. A position adjuster can be used to move ES probe assembly such that any ES tip can be located near the ES source centerline. With this device several sample solutions can be rapidly analyzed with little or no cross contamination which can occur when multiple samples are delivered to the ES source sequentially through the same ES probe tip. Although the system described above is intended for introduction of the samples to the vacuum chamber of the mass spectrometer from the atmospheric pressure chamber, the API system described above is not designed for automatically inputting and outputting each of the sample supports into and from the sample receiving chamber of the mass spectrometer. The system is rather intended for individual introduction of sample supports one-by-one in a slow sequence and therefore does not need means for automating loading or unloading of ES tips. The ampoule-like construction of the ES-tips itself is not suitable for quick introduction of the sample into the mass spectrometer, as compared to the use of a multiple-cell sample plates.

Agilent Technologies Inc. introduced an AP-MALDI, co-developed by Masstech, Inc., by providing a sample handling interface and a laser that is capable of handling and analyzing a sample plate with multiple samples. This interface with little or no modification can be attached to various atmospheric pressure ionization mass spectrometers such as an ion-trap type, and a time-of-flight mass spectrometers. In this apparatus, a substrate plate with deposited samples is manually loaded on a target flange that is equipped with positioning x-y stage. The x-y stage is used to move the sample plate with respect to the mass spectrometer sampling orifice to analyze samples deposited on the plate. The main disadvantage of the apparatus is the inconvenience of manual loading for sample plates. The autosamples, which are designed for the conventional vacuum MALDI, are too complicated and inefficient for AP-MALDI since they are designed for delivering of the sample plates into the vacuum. Also robotic systems used in stamping or welding industries with a flexible arm can be used to load the sample plates, into a commercial apparatus produced by Masstech, Inc., however these systems are complex and not designed to work directly with plates that have biological sample deposited on one side of the plate. For example, for picking up plates several commercial robotic systems use vacuum grips that can destroy or contaminate the deposited sample.

Thus, it has been shown that in all known systems of sample analysis equipped with automatic or semi-automatic sample plate loading and transportation mechanisms the grippers of these mechanisms come in physical contact directly with the sample plate that carriers the samples. This condition creates possibility for contamination of the samples and sample plates.

OBJECT AND SUMMARY OF THE INVENTION

It is an object of the present invention to provide an apparatus for automated sample analysis by MALDI mass spectrometry, wherein the number of contacts between the sample plate and a sample plate handling mechanism is reduced due to the use of an intermediate sample plate carrier for carrying and handling the sample plates prior to loading them to the working station of the mass spectrometer.

It is another object to provide a moveable and disconnectable sample-plate handling flange, which is docked to the orifice inlet port of the mass spectrometer during loading of the samples to the mass spectrometer and is provided with an additional function of transfer of the sample plates from the storage cassette to the mass spectrometer. It is another object of the invention to provide the apparatus of the aforementioned type with sample plates carriers that are used as an intermediate sample plate carriers for carrying the plates to a pick-up station and that circulates between the aforementioned station and a sample plate carrier storage device.

The apparatus of the invention consists of two module, one of which carries sample-plate handling flange, which is docked to the mass spectrometer in a working position for loading ionized samples from the atmospheric pressure environment to the to the mass spectrometer, while the other one is used for picking up the sample plate carriers with preliminarily prepared sample plates from the storage cassette and for transferring the aforementioned carriers to a stand-by position for disconnection of the sample plates from the carriers and for deliver them to the mass spectrometer. The sample-plate handling flange is disconnectable from the mass spectrometer and moveable between the aforementioned working position and the stand-by position and is provided with means for taking the stand-by sample plate from the plate carrier and for holding the plate with samples during delivery of the ionized samples to the mass spectrometry. The sample-plate handling flange is also provided with means for shifting the sample plate inside the sample-plate handling flange in the X-Y coordinate system for arranging a selected sample cell coaxially with the center of the ion-sampling orifice. The first module provides movements in the Z-axis and X-axis directions, and the second module provides movements in the Z-axis and Y-axis direction. As the mechanisms of the aforementioned modules operate under atmospheric pressure, they do not need the use of any special and expensive sealing devices required for use of similar mechanisms in vacuum. The system is fully automated and movements of all mechanisms and drives are controlled by a data preliminarily inputted to a central processing unit provided in the control system of the apparatus.

DETAILED DESCRIPTION OF THE INVENTION

Figure 1:
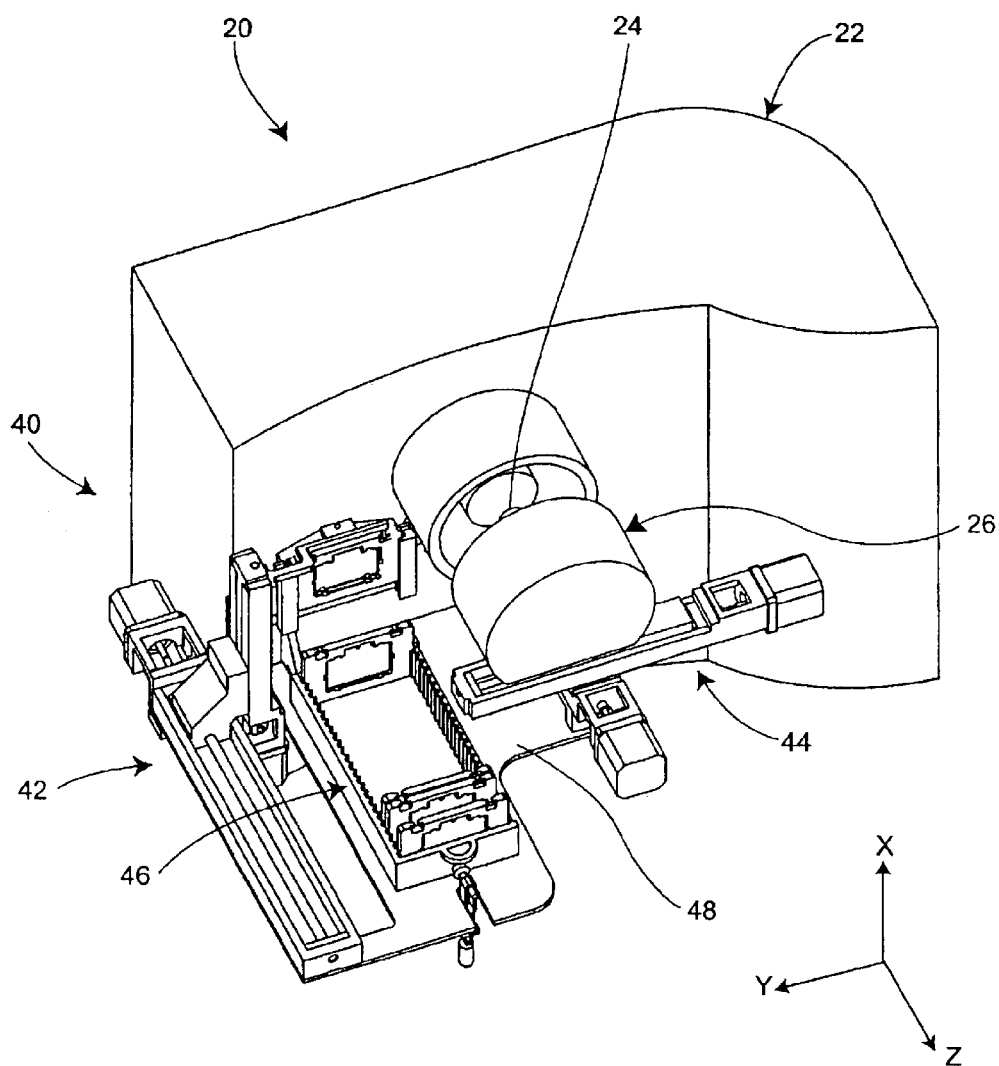
FIG. 1 is a general three-dimensional view of the apparatus of the present invention for sample analysis by atmospheric pressure ionization matrix assisted laser desorption ionization.

A general three-dimensional view of the apparatus of the present invention for sample analysis by atmospheric pressure ionization matrix assisted laser desorption ionization (hereinafter referred to as a AP-MALDI) mass spectrometry is shown in FIG. 1. As can be seen from this drawing, the apparatus, which in general is designated by reference numeral 20, consists of the following major units which are shown in FIG. 1 without description of the details and which will be described separately in more detail in the subsequent description. Thus, the apparatus of the invention 20 consists of a AP-MALDI mass spectrometer 22 with an ionization chamber 23 having an ion-sampling orifice 24, a sample-plate handling flange (hereinafter referred to merely as a target flange) 26, that comprises a disconnectable part of the ionization chamber 23 moveable away therefrom for handling and loading/unloading the sample plates, and a base plate 48 with a first drive module 42 and a second drive module 44. Thus, in contrast to any known ionization chambers of this type, the ionization chamber 23 of the apparatus 20 of the invention is divisible and consists of a stationary portion 25 (FIG. 1) that belongs to the mass spectrometer 22 and a moveable part, i.e., the target flange 26 that is completely disconnectable from the permanent portion 25 and that handles and transfers sample plates, such as a sample plate 26-1a shown in FIG. 1. directly from the protective sample plate carriers, such as a sample plate carrier 26-3 (FIG. 1) to the mass spectrometer 22. It is important to note that during transportation of the sample plates between the target flange 26 and the storage device, which is described below, the sample plates are located in protective positions within the sample plate carriers. In FIG. 1 the sample plate 26-1a, as well as all other sample plates, is shown in a protective position so that only the back side 261-1a of each of the sample plates is seen in this drawing. The mass spectrometer 22 and the AP-MALDI system used in conjunction with the mass spectrometer 22 may be of any appropriate type and do not constituted the subject of the present invention. For example, the mass spectrometer may be of a time-flight type described in the prior art section, or of any other type. For convenience of the subsequent description, let us introduce a three-axis system of orthogonal coordinates. As can be seen from FIG. 1, the target flange is arranged in a plane formed by axes X and Y. The axis of the ion-sampling orifice 24 is parallel to axis Z. The first module 42 provides movements in the direction of axes X and Z, and the second module 44 provides movements in the direction of axes Z and Y.

The base plate 48 that supports the modules 42 and 44 is preferably mounted directly onto the mass spectrometer 22 to provide stable registration between the target flange 26 and the mass spectrometer ion-sampling orifice 24. In FIG. 1, reference numeral 46 a sample plate storage, which is shown conventionally without details which will be described later.

Figure 2:
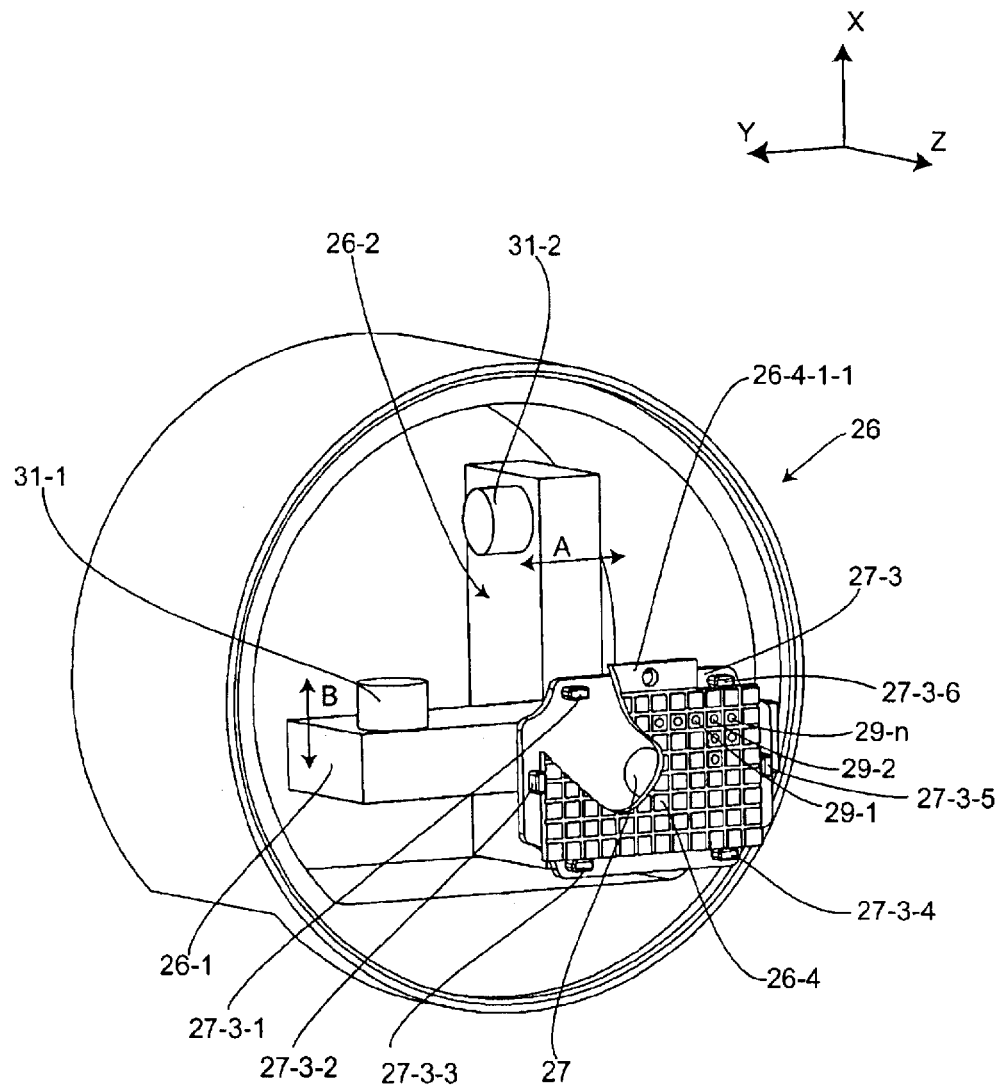
FIG. 2 is a three-dimensional view of the target flange of the apparatus of the invention, which is equipped with separate moveable, mutually perpendicular stages for displacement of the sample plate inside the sample-plate handling flange.

FIG. 2 is a three-dimensional view of the target flange 26, which is equipped with separate moveable, mutually perpendicular stages 26-1 and 26-2. The view of FIG. 2 is seen from the mass-spectrometer side. The stage 26-1 supports a sample plate gripper 27-3 with a magnet 27, e.g., an electromagnet for holding that, in turn, supports a sample plate 26-4 with samples 29-1, 29-2, . . . 29-n deposited on the sample plate 26-4 for analysis. Furthermore, for alignment and retaining of the sample plate 26-4 in the target flange 26, the sample plate gripper 27-3 is provided with gripping fingers 27-3-1, 27-3-2, 27-3-3, 27-3-4, 27-3-5, and 27-3-6. These gripper fingers are also may be used for aligning sample carriers 26-3 which will be described later with reference to FIG. 7.

Although in FIG. 2 the sample plate 26-4 is shown with samples 29-1. 29-2, . . . 29-n exposed to the outside, this is the final working position of the sample plate, in which it is installed on a sample plate table formed by the stages 26-1, 26-2 and the target flange 26. However, as shown in FIG. 1. during storage and transportation through the atmospheric environment to the target flange 26, the sample plates, such as, e.g., a sample plate 26-1a, assume positions, in which the samples 29-1, 29-2, . . . 29-n (not shown in FIG. 1 are unexposed to the surrounding atmosphere as they face the sample plate carrier 26-3. Therefore, the samples are protected from contamination. Another feature that also contributes to the protection of the samples from contamination is that the sample plate handling mechanism does not have direct contact with the sample plate but rather with the protective sample plate carrier. This allows handling and transportation of the sample plates within apparatus of the present invention with the samples in an atmospheric pressure environment, i.e., without the use of a specially controlled environment such as vacuum used in conventional systems of this type.

The stage 26-1 is moveable on the stage 26-2 in the direction of arrow B, which is parallel to the direction of axis X in FIG. 1, i.e., vertically and perpendicular to the axis Z of the ion-sampling orifice 24 (FIG. 1). This movement can be carried out by a motor 31-1. The stage 26-2, in turn, is moveable in the direction A, which is parallel to the direction of axis Y in FIG. 1, i.e., perpendicular to the direction of arrow B as shown in FIG. 2. This movement can be carried out by a motor 31-2. Description of the drive mechanisms for the aforementioned movements is omitted since these mechanisms are beyond the scope of the present invention and since the mechanisms of the aforementioned type are known and commercially produced by MassTech Inc., MA, USA (see http://www.apmaldi.com/Products). The above-described mechanism for moving the sample plate within the target flange 26 allows positioning of any sample (29-1, 29-2, . . . 29-n) of the sample plate 26-4 coaxially with the center of the ion-sampling orifice 24 (FIG. 1). The aforementioned sample cells are loaded with samples, e.g., in the form of matrices with analytes, in a manner known in the art. Thus, the x-y drive system formed by the stages 26-1, 26-2 allows for aligning of any cell with the position of the mass spectrometer ion-sampling orifice 24 (FIG. 2) for producing ions from the analyzed sample, e.g., with the use of laser radiation.

One distinguishing feature of the present invention is that the sample plates are not always handled directly but are handled through the intermediary of the aforementioned sample plate carriers, such as, e.g., the sample carrier 26-3 shown in FIG. 1, that circulate through the system between the sample storage device and the sample plate loading/unloading station or stations. As will be shown below, the sample plate carrier of the invention may carry one or a plurality of sample plates and may perform linear or rotary motions for transporting the carriers with sample plates to the working position. As the sample plate handling mechanism does not have direct contact with the sample plate but rather with the sample plate carrier, the chance of contamination of the samples and sample plates is reduced.

In accordance with the invention, the target flange 26 functions not only as a sample plate support and the coordinate positioner, but also as a gripper for picking up the sample plates from the sample plate carrier storage 46, as well as for transporting the sample plates and for aligning the sample cells relative to the spectrometer ion-sampling orifice 24. Therefore, first it is necessary to consider the aforementioned transportation system 40 for sample plates and sample carriers shown in a three-dimensional general view in conjunction with the mass spectrometer 22 in FIG. 3.

Figure 3:
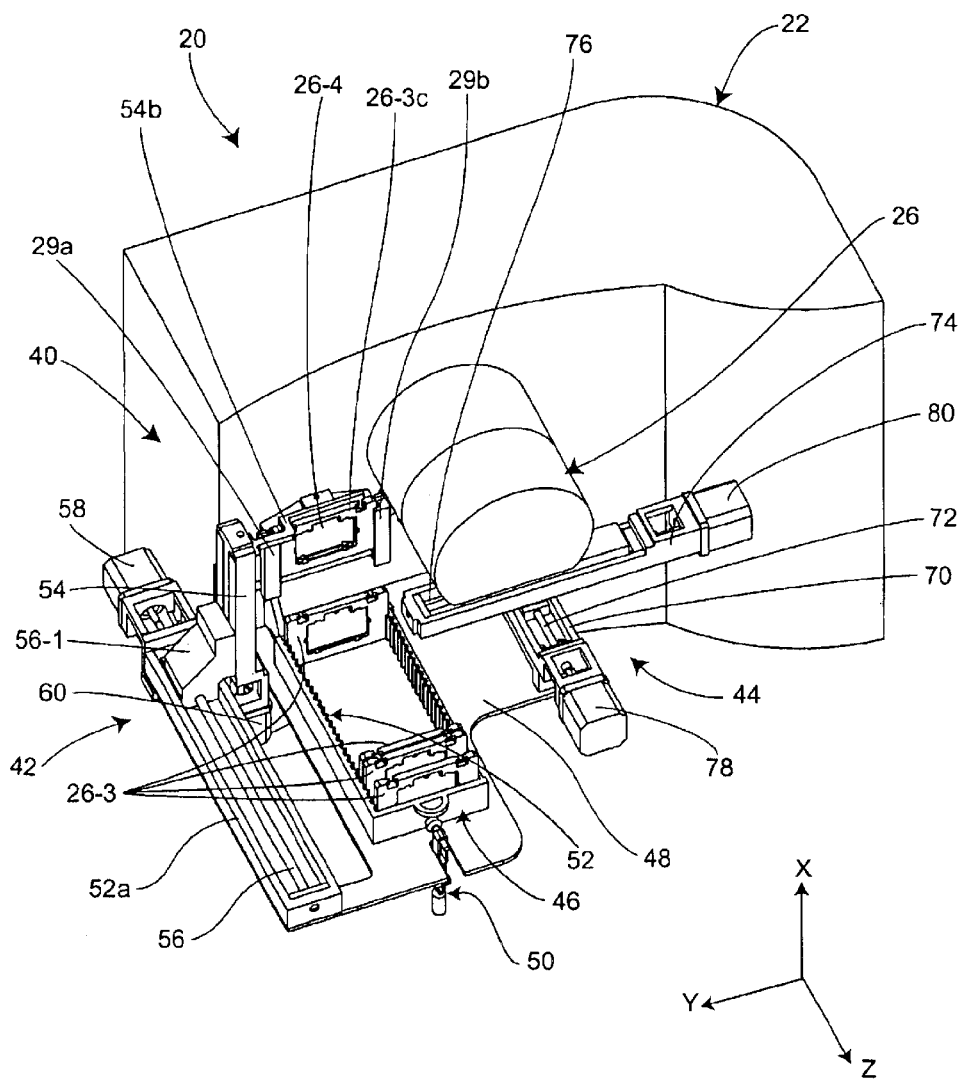
FIG. 3 is a general three-dimensional view of the entire apparatus of the invention with the sample-plate handling flange in a working position, in which the center of the sample plate is aligned with the center of the ion-sampling orifice.

As shown in FIG. 3, which is a general three-dimensional view of the entire apparatus according to one embodiment of the invention, the sample-carrier transportation system 40 consists of two aforementioned main modules 42 and 44.

The first module 42 is intended for unloading/loading of the sample plate carriers, such as the sample plate carrier 26-3 shown in FIG. 3, from and into the cassette 46. Each sample plate carrier 26-3 carries a sample plate 26-4 (FIG. 3) with samples for analysis. The sample plate 26-4 can be preliminarily inserted into the sample plate carriers 26-3 manually or automatically at a separate remotely located station.

As shown in FIG. 3, the cassette 46 extends in the direction parallel to Z-axis (FIG. 1), and the sample plate carriers 26-3 are arranged in the slots 52 of the cassette 46 in positions parallel to the X-Y plane formed by the X-axis and Y-axis.

The assembly 42 has a base platform 48 that supports the cassette 46 which can be clamped in a required position by a quick-release clamp 50, which presses the cassette 46 against a stopper (not shown). The cassette 46 has the shape of a rectangular box with an open upper side and is divided into a plurality of sections by guide slots 52 for insertion of individual sample plate carriers 26-3. In the embodiment of the invention shown in FIG. 3, the cassette 46 has an elongated shape extending in the direction parallel to axis Z. The base platform 48 may be rigidly connected to the housing of the mass spectrometer 22 or may be supported by a separate pedestal (not shown in the drawings).

The module 42 is further provided with a Z-direction guide mechanism, which consists of guide rail 52a for guiding an L-shaped bracket 54 in the direction of Z-axis. For this movement, the module 42 is provided with a lead screw 56 driven into rotation from a stepper motor 58 controlled from a computer (not shown). The lead screw 56 engages a nut (not shown) fixed in the base 56-1 of the vertical leg 54a of bracket 54. The vertical leg 54a is arranged in the direction of axis X and supports a horizontal leg 54b, which is moveable in the X-axis direction along the vertical guide rail (not shown), which is formed on the side surface of the vertical leg 54a and have a configuration similar to the guide rail 52a. The horizontal leg 54b is driven from a computer-controlled stepper motor 60 via a lead screw and nut mechanism (not shown in FIG. 3) similar to the one used for driving the vertical leg 54a in the Z-axis direction.

Figure 7:
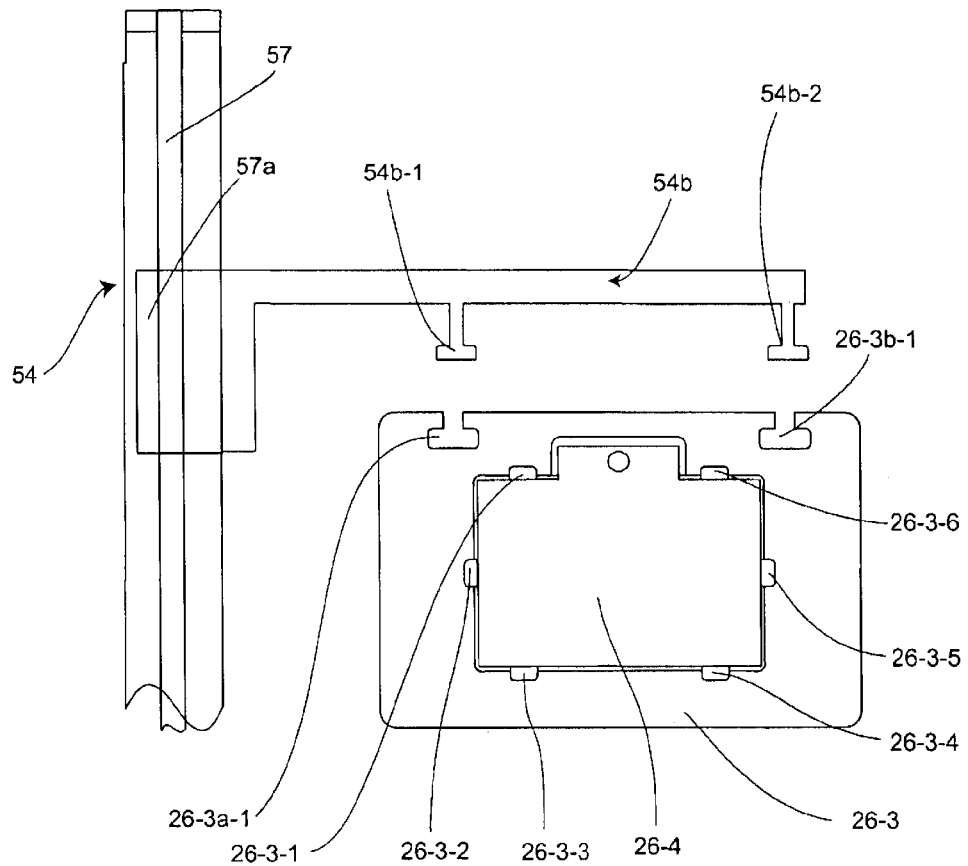
FIG. 7 is a partial view of the horizontal leg and the sample plate carrier illustrating arrangement of the T-shaped projections on the horizontal leg and T-shaped slots on the sample plate carrier.

As can be seen from FIG. 7, which in more detail is explained later, each sample plate carrier 26-3 has reversed T-shape slots 26-3a-1 and 26-3b-1, while the horizontal leg 54b (FIG. 3) has complementary T-shaped projections 54b-1 and 54b-2. Since with the use of the stepper motors 58 and 60 (FIG. 3) the horizontal and vertical legs 54a and 54b can be arranged in any required position, the T-shaped projections 54b-1 and 54b-2 may approach the slots 26-3a-1 and 26-3b-1 of an appropriate sample plate carrier 26-3, may be aligned with the position of these slots, introduced into the slots by a short movement of the T-shaped projections 54b-1 and 54b-2 in the Z-axis direction, and then moved up in the direction of axis X for extracting the sample plate carrier 26-3 from the slots 52 of the cassette 46 and for delivery thereof to the position which in FIG. 3 is shown above the cassette 46 in the uppermost position of movement in the direction of X-axis and in the extreme left position along the Z-axis. In order to perform the above-described operations of picking up of the sample plate carrier 26-3 from an arbitrary position of the carrier in the cassette 46, the sample plate carriers 26-3 should have space sufficient for insertion of the aforementioned T-shaped projections 54b-1 and 54b-2 between the sample carriers 26-3.

The aforementioned extreme upper and leftward position is a stand-by position of the sample plate carrier from where the sample plates held by the carriers are ready for transfer to the aforementioned second module 44. In order to align the sample plate carrier 26-3 located in the stand-by position with the gripper 27-3 of target flange 26, the sample plate carrier is provided with alignment openings 26-3-1, 26-3-2, 26-3-3, 26-3-4, 26-3-5, and 26-3-6. These openings are intended for engagement with the aforementioned gripper fingers 27-3-1, 27-3-2, 27-3-3, 27-3-4, 27-3-5, and 27-3-6 shown in FIG. 2.

Similar to the first module 42, the second module 44 also has mechanisms for movement in two mutually perpendicular axes, i.e., the Z-axis and the Y-axis. More specifically, the Z-movement mechanism has a guide rail 70, which is supported by the base platform 48 and is arranged in the direction parallel to Z axis. The guide rail has a lead screw 72, which engages a nut (not shown) fixed in guide rail 74, which is extended in the Y axis direction and also is provided with a lead screw 76 extending in the Y axis direction. The Z-drive mechanism is driven from a computer-controlled stepper motor 78, while the Y-drive mechanism is driven from a computer-controlled stepper motor 80. The lead screw 76 engages a nut fixed in the target flange 26, so that, with the use of the aforementioned Y-drive and Z-drive mechanisms, the target flange 26 can be placed into any position in the plane Y-Z and can be linearly shifted in the direction of axis Y. In other words, as shown in FIG. 4, the target flange 26 can be aligned with the sample plate 26 in the aforementioned stand-by position shown in FIG. 3.

Figure 5:
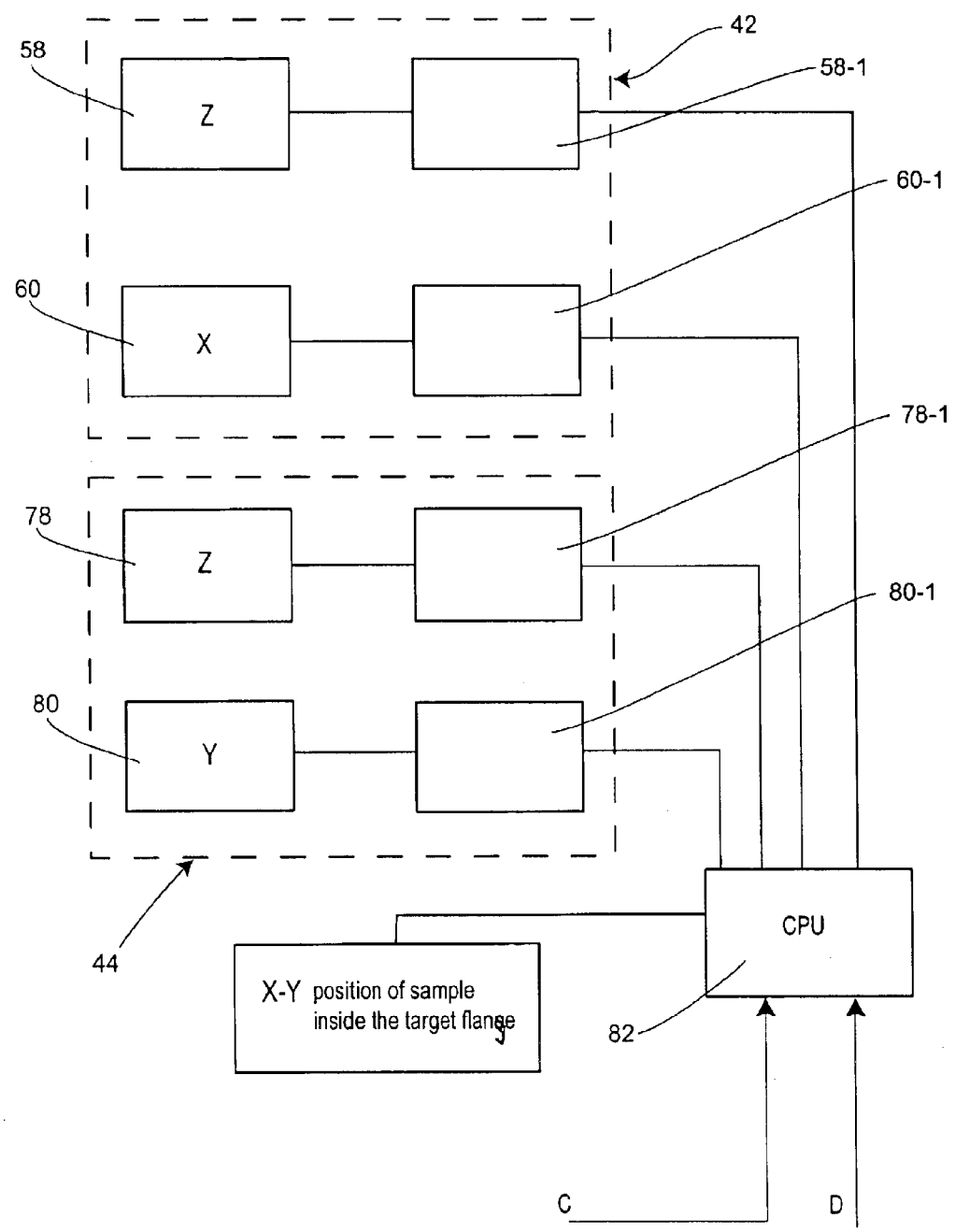
FIG. 5 is a block diagram of the control system used in the apparatus of the invention.

The block diagram of the control units that control operational sequence and movements of the mechanisms of the system 40 is shown in FIG. 5. The control system contains a central processing unit (CPU) 82 which is connected to the Z-axis stepper motor 58 and the X-axis stepper motor 60 of the module 42, as well as to the Z-axis stepper motor 78 and the Y-axis stepper motor 80 of the module 44. The control of the aforementioned stepper motors 58, 60, 78, and 80 is carried out through drivers 58-1, 60-1, 78-1, and 80-1, respectively. Arrows C and D designate data input lines for inputting data to the CPU 92. These data may comprise positions (coordinates) of the sample plate carriers 26-3 in respective cassettes 46, sequence of operation of the aforementioned stepper motors in the assemblies 42, 44, sequence and positions for unloading the sample plates after the completion of the analysis, time of treatment and stand-by, etc. The CPU also contains data for positioning the cells of the sample plate 26-4 in the X-Y coordinate system coaxially with the center of the ion-sampling orifice 24 (FIG. 1).

The AP-MALDI mass-spectrometer system of the invention, shown in FIGS. 1–4, operates as follows.

Figure 4:
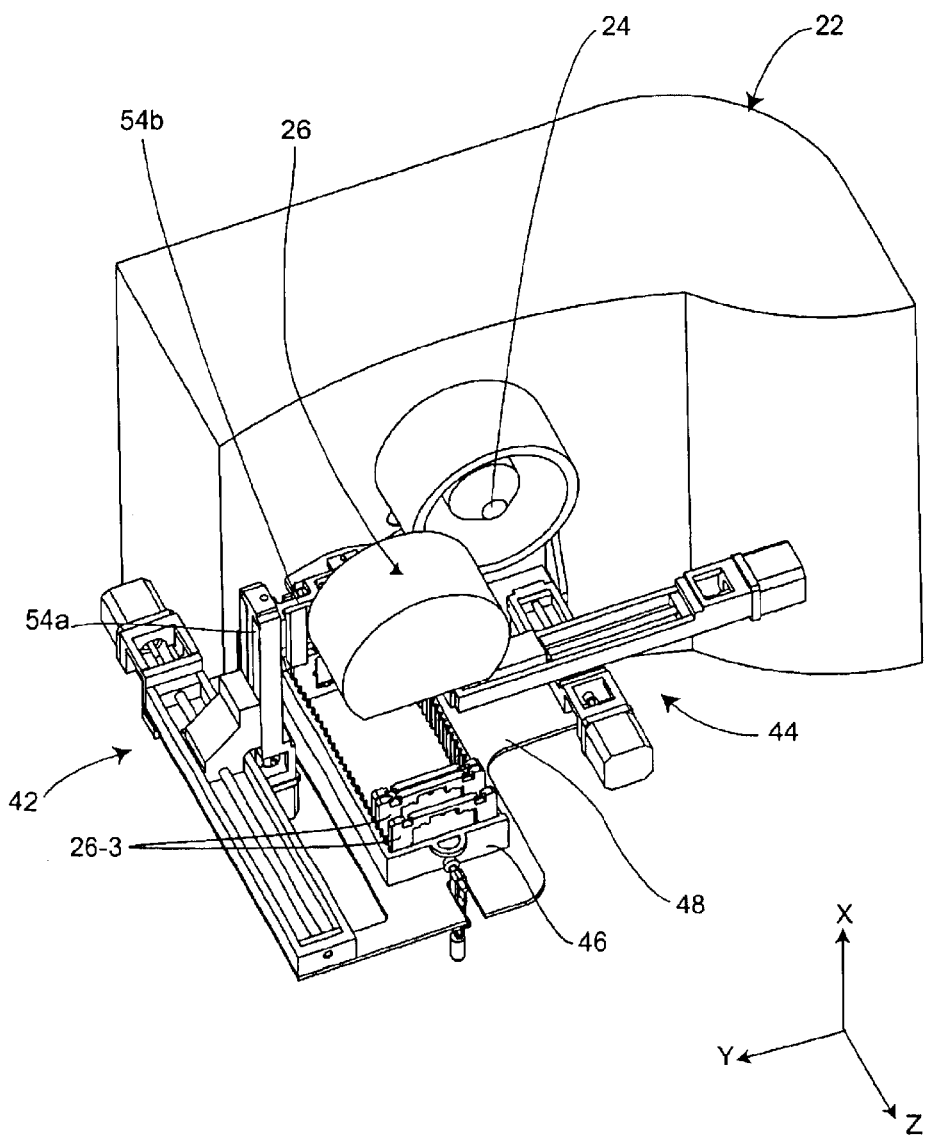
FIG. 4 is a general three-dimensional view of the entire apparatus of the invention with the sample plate carrier in a stand-by position, from where the sample plate it is taken by the target flange for transfer to the ion-sampling orifice.

The preparatory operations associated with loading of the samples into individual cells of the sample plates 26-4, insertion of the sample plates 26-4 into the sample-plate carriers 26-3, and insertion of the loaded sample-plate carriers 26-3 into the cassette 46 can be carried out at an outside location, and the cassette 46 filled with the loaded sample plate carriers 26-3 is secured in the working position shown in FIGS. 3 and 4 by clamping it in place on the base platform 48 with the use of the quick-release clamp 50.

The programs that control operation of the system 40 from the central processing unit CPU 82 may perform operations of the assemblies 42 and 44 in sequence or simultaneously. For simplicity of the description, let us consider sequential operation of the assemblies 42 and 44. In accordance with this mode of operation, the CPU 82 sends a command to the driver 58-1 of the stepper motor 58, which initiates the movement of the entire L-shaped bracket 54 in the Z-axis direction by rotating the lead screw 56 that engages the nut (not shown) fixed in the vertical leg 54*a*.

Figures 6A, 6B, 6C, 6D:
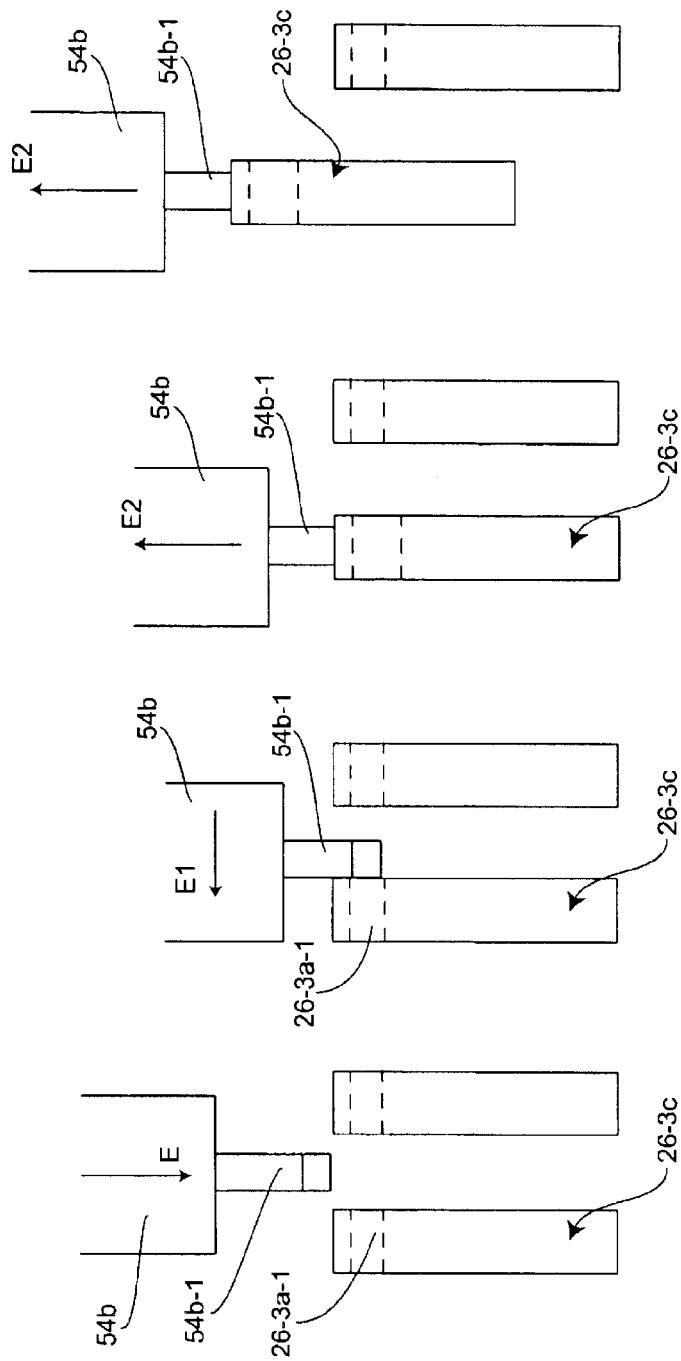
FIGS. 6a–6d are partial views illustrating the sequence of operations associated with picking up of the sample plate carrier from the cassette.

The sequence of operations associated with picking up of the sample plate carrier 26-3 from the cassette 46 (FIG. 3) is shown in FIG. 6. When the T-shaped projections 54*b*-1 of the horizontal leg 54*b* of the bracket 54 reach the position above the space between the sample plate carrier 26-3*c* that has to be picked up and the adjacent sample plate carrier 26-3*d* (FIG. 6*a*), the aforementioned movement of the bracket 54 in the Z-axis direction is discontinued, and the CPU 82 sends a command to the driver 60-1 of the X-axis stepper motor 60. As a result, the horizontal leg 54*b* begins to move in the direction of axis X (shown by the arrow E in FIG. 6*a*). This movement is carried out by rotating a lead screw 57 shown in FIG. 7, which is a partial view of the horizontal leg 54 with the guide and drive members. The lead screw 57 engages a nut 57*a*, which is a rigidly attached to the horizontal leg 54*b* of the bracket 54. The lead screw and nut mechanism of the horizontal leg 54*b* are similar to the same elements of the mechanism for driving the vertical leg 54*a* in the Z direction from the stepper motor 58.

The downward movement of the horizontal leg 54*b* in the direction of arrow E (FIG. 6*a*) is continued unit the T-shape projections 54*b*-1 are aligned with the positions of the complementary T-shaped slots 26-3*a*-1 (FIG. 6*b*). Next the CPU 82 send a command to the driver 58-1 for starting the stepper motor 58 (FIG. 3) that performs short displacement of the horizontal leg 54*b* for insertion of the projections 54*b*-1 into the T-shaped slots 26-3*a*-1 (FIG. 6*c*) in the direction of arrow E1. The next step is raising the horizontal leg 54*b* with the caught sample plate carrier 26-3*c* (FIG. 6*d*) in the direction of arrow E2. This movement in the direction of X-axis is continued until the horizontal leg 54*b* reaches the extreme upper position shown in FIG. 3. In this condition, the sample plate carrier 26-3*c* is maintained in a stand-by position until this sample plate is taken by the target flange 26 of the module 44 as described below.

When the sample plate carrier 26-3*c* is held in the stand-by position shown in FIG. 3, the CPU 82 sends a command to the driver 78-1 (FIG. 5) of the stepper motor 78 of the module 44. The stepper motor 78 begins to rotate, whereby rotation of the lead screw 72 via engagement with the nut (not shown) causes translational movement of the guide rail 74 in the direction of the Z-axis. As a result, the target flange 26 is moved away from the docked position with the mass spectrometer 22.(FIG. 3) to a predetermined Z-position. Under control of the CPU 82, the target flange 26 can freely move in the direction of Y-axis without interference with the horizontal leg 54*b* of the module 42 that supports the sample plate carrier 26-3*a* maintained in the stand-by-position.

The next step of the operation of the system 40 is the transverse movement of the target flange 26 in the Y-axis direction towards the sample plate 26-4 supported by the sample-plate carrier 26-3*a*. This movement is carried out by energizing the stepper motor 80 under a command sent from the CPU 82 to the driver 80-1 of this motor. The aforementioned movement in the Y-axis direction is continued until the center of the target flange 26 is aligned with the center of the sample plate 26-4 held in the stand-by sample plate carrier 26-3*a*. This position is shown FIG. 4.

The sample plate 26-4 is taken from the horizontal leg 54*b* of the bracket 54 by the electromagnet 27, which is energized by a command from the CPU 82, when the target flange 26 is aligned with the sample plate 26-4. As a result, the sample plate 26-4 is attracted by the electromagnet 27 (FIG. 2) and is disconnected from the sample plate carrier 26-3, which remains in the stand-by position shown in FIG. 3. The sample plate carrier 26-3 is held in the aforementioned stand-by position and is prevented from extraction by the target flange 26 by means of shoulders 29*a* and 29*b* (FIG. 3) on the horizontal leg 54*b*.

After the sample plate 26-4 is taken by the target flange 26, the stepper motor 80 receives from the CPU 82 via its driver 80-1 a command for returning the target flange 26 to the position of alignment with the center of the ion-sampling orifice 24 shown in FIG. 3. In other words, the target flange 26 is moved in the Y-axis direction away from the bracket 54 of the module 42. Upon alignment of the center of the sample plate 26-4 with the center of the ion-sampling orifice 24 of the mass spectrometer 22, the CPU sends an appropriate command to the driver 78-1 of the Z-axis stepper motor for initiation of the movement of the guide rail 74 together with the target flange 26 towards the ion-sampling orifice 24. This movement is continued until the target flange 26 comes into docked contact with the orifice inlet port 24*a* (FIG. 1). Now the sample plate 26-4 is in a working position ready for initiation of mass-spectrometry analysis in a manner known in the art, as has been described earlier.

Upon completion of the mass-spectrometry analysis, all the operations described above are repeated in a reverse order up to insertion of the analyzed sample plate 26-4 to the same slot of the cassette 46 or to any other location as requested by the command of the CPU 82.

Meanwhile, during transportation of the sample plate 26-4 and processing of the samples supported by this plate, the sample plate carrier 26-3*c* located in the stand-by position shown in FIG. 3 is waiting in the stand-by position for the return of the processed sample plate 26-4. The return of the sample plate carrier is carried out in a sequence reverse to the movement of the sample plate carrier in the direction away from the cassette.

Although the operation of the assemblies 42 and 44 were described in sequence, it is understood that movements of the mechanisms of these assemblies can be carried out simultaneously or partially simultaneously under the appropriate commands of the CPU. These commands prevent interference or collision of the moving parts. Furthermore, for acceleration of the movement and for shortening the cycle time, the movements in the direction of mutually perpendicular axes can be carried out simultaneously in the same module. For example, in the module 44, the movement of the sample flange 26 along the axis Z can be carried concurrently with the movement of the sample flange along the axis Y.

Figure 8:
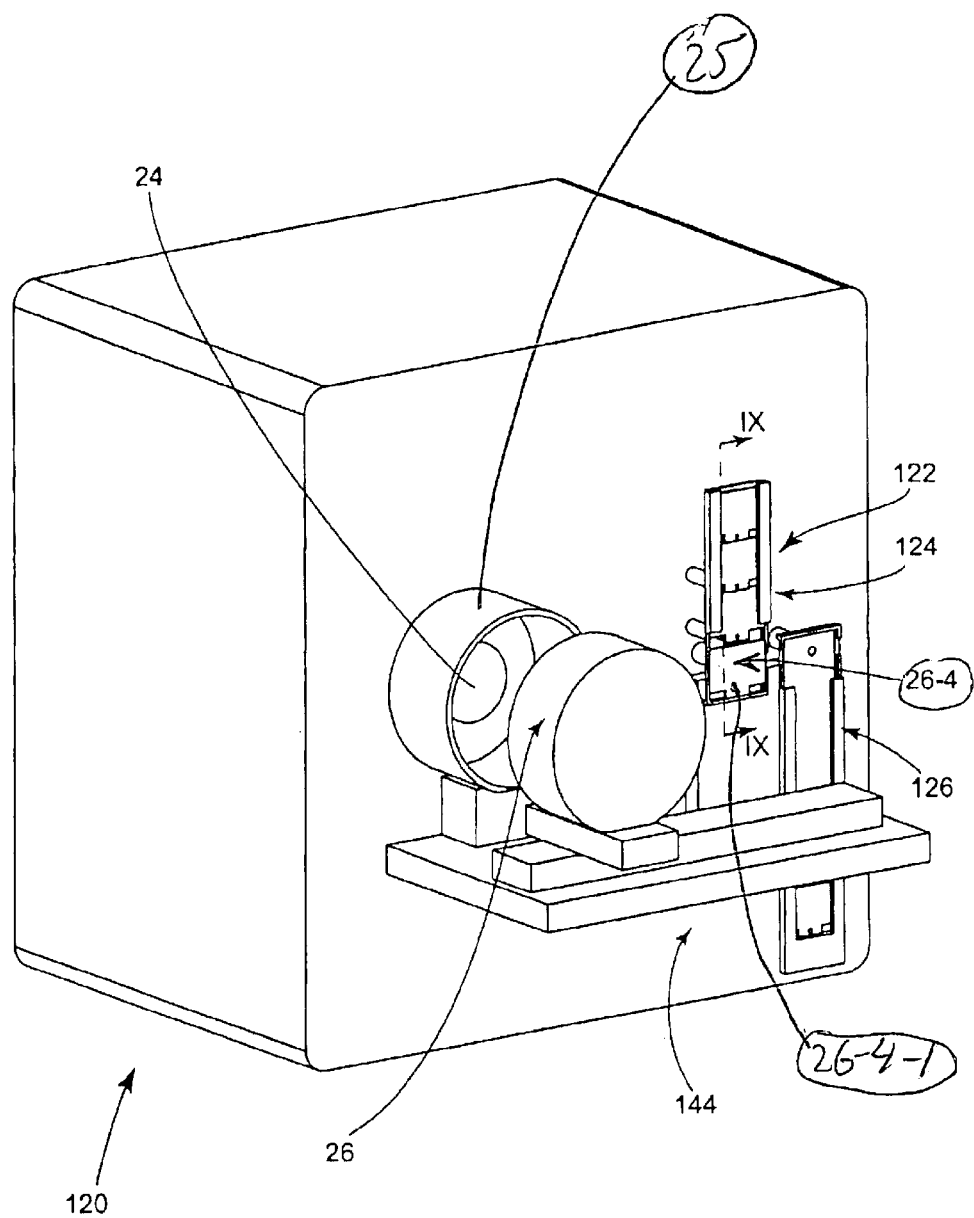
FIG. 8 is a general three-dimensional view of an apparatus made in accordance with another embodiment of the present invention, wherein the sample-plate handling flange is used in conjunction with a loading and unloading replaceable cartridge-type sample plate carriers.

The main principle of the present invention that consists of utilizing the target flange as a combined means for loading/unloading sample plates into and from the mass spectrometer and for holding the sample plates in sample plates carriers during transportation and handling will not be violated if the apparatus of the invention incorporates only one sample handling module. FIG. 8 is a general three-dimensional view of an apparatus made in accordance with a second embodiment of the present invention, wherein the target flange is used in conjunction only with one sample plate carrier handling module that supports two sample plate carriers with a plurality of sample plates in each of the carriers. In the description of this embodiment, the parts and units identical with those described in the previous embodiment will be designated by the same reference numerals.

The apparatus 120 shown in FIG. 8 consists of a conventional mass spectrometer 22, e.g., of an ion-trap type, with an ion-sampling orifice 24 for producing ions from the analyzed sample, e.g., with the use of laser radiation. The apparatus 120 is provided with a sample storage device 122, which consists of a sample plate loading carrier 124 for loading the sample plates 26-4 (FIG. 2) to the target flange 26 and a sample plate unloading carrier 126 for unloading the processed sample plates 26-4 from the target flange 26. Once again, it can be seen from FIG. 8 that in this embodiment during loading and unloading the samples of the sample plates 26-4 on their back sides 26-1 are exposed to the atmospheric pressure, while the sample sides 26-1 are not exposed to the atmosphere pressure but face the loading and unloading carriers 124 and carrier 126, respectively.

The construction of the target flange 26 shown in FIG. 8 is the same as of the one described in the previous embodiment with the exception that a permanent magnet is used instead of the electromagnet 27 (FIG. 2).

As shown in FIG. 8, the sample plate loading carrier 124 and the sample plate unloading carrier 126 are made in the form of two vertical parallel cartridges that are arranged side by side and can be attached to the housing of the mass spectrometer 22, fixed to another stationary object, or stand independently. The loading carrier 124 can be loaded with a plurality of sample plates 26-4 at a remote station and installed on the mass spectrometer 22. The function of the aforementioned carrier is to load (for the loading carrier-124) and to receive (for the unloading carrier 126) the appropriate sample plates 26-4 (FIG. 2) from the carrier to the target flange 26 (for the loading carrier 124) and from the target flange 26 to the carrier (for the unloading carrier 126). In general, the constructions of both carriers are similar. The construction of the sample loading carrier 124 is shown in FIG. 9, which is a vertical sectional view along the lines IX-IX but with the target flange in a position aligned with a sample plate in the loading carrier.

Figure 9:
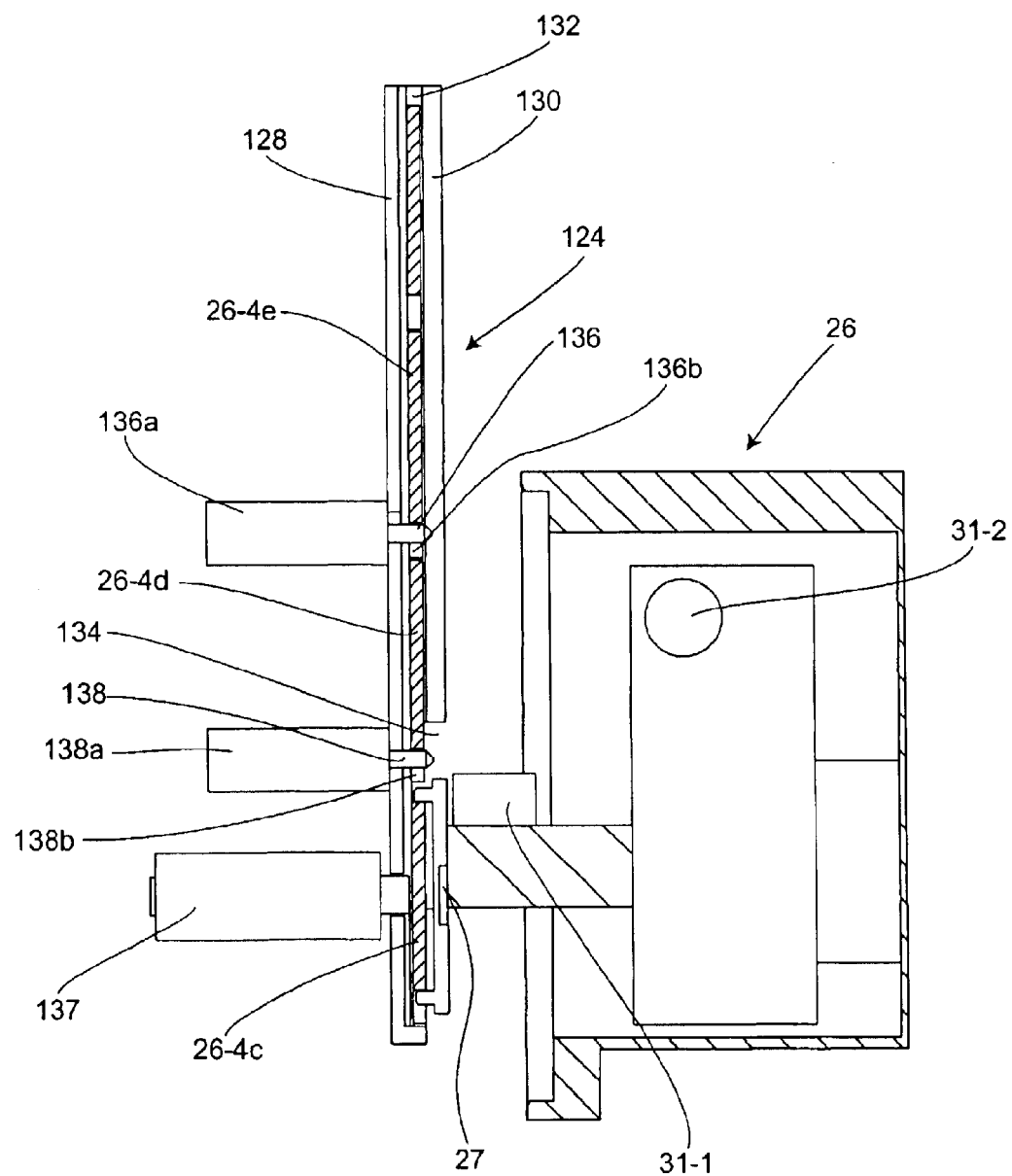
FIG. 9 is a vertical sectional view along the lines IX—IX but with the target flange in a position aligned with the sample plate loading position.

As can be seen from FIG. 9, the carrier 124 comprises a pair of vertically arranged parallel elongated plates 128 and 130 with a guide channel 132 formed between them for guiding sample plates 26-4 inserted into the guide channel 132 so that they are stacked one onto the other with vertical orientation of the carrier planes. The plate 130 that faces target flange 26 has a window 134, which is aligned with the target flange 26 in a position of FIG. 9, in which the magnet 27 picks up the lowermost sample plate 26-4 of the carrier 124 and holds it in the target flange 26 for subsequent handling and processing.

In order to provide one-by-one feeding of the sample plates from the top of the carrier to the lowermost, i.e., target flange loading position, the carrier 124 is provided with a couple of alternatingly operating solenoid-controlled lock pins 136 and 138. Each pin 136 and 138 is driven in the direction perpendicular to the planes of the sample plates by respective solenoids 136a and 138a controlled from the CPU 82 (FIGS. 5 and 9). Each pin 136 and 138 is used as a stopper against the shoulder openings 136b and 138b formed between the sample plates 26-4c and 26-4d. The control from the CPU 82 is carried out so that when the pin 138 is withdrawn away from the shoulder opening 138b by the action of the solenoid 138a, the sample plate 26-4d falls under gravity to a loading position where it is held by the electromagnet 137. Meanwhile, the pin 136 is inserted into the shoulder opening 136b the sample plate 26-4e, and all the remaining sample plates located above the plate 26-4e. The lowermost sample plate 26-4c positioned in the window 134 can be extracted from the carrier by the magnet 27 the target flange 26, while the electromagnet 137 is deactivated by the CPU 82.

The magnet 27 extracts the sample plate 26-4c from the carrier through the window 134 when the target flange 26 is moved to the position of FIG. 9, i.e., when the center of the target flange 26 is aligned with the center of the sample plate 26-4. The drive mechanism used for movement of the target flange carrier between the position of alignment with the center of the orifice 24 (FIG. 1) and the center of the sample plate 26-4 is carried out by means of the same mechanism as the module 44 (FIG. 3) of the embodiment of the apparatus shown in FIG. 3.

Similar to the first embodiment, the module 144 of the embodiment of FIG. 8 also has mechanisms for movement in two mutually perpendicular axes, i.e., the Z-axis and the Y-axis. As these mechanisms are identical to those described above, their consideration for this embodiment is omitted. The module 144 operates in the same manner as the module 44 of the previous embodiment with the only difference that instead of aligning with the stand-by position of the first module 42, the module 144 is aligned either with the center of the lowermost sample plate located in the carrier 124 of the second embodiment, or with the center of the receiving position on the unloading carrier 126. In the second embodiment, the CPU 82 controls movements of the target flange between three positions: 1) position of alignment with the lowermost sample plate located in the loading carrier 124; 2) position of alignment with orifice of the mass spectrometer; and 3) position of alignment with the receiving window of the unloading carrier 126.

Figure 10:
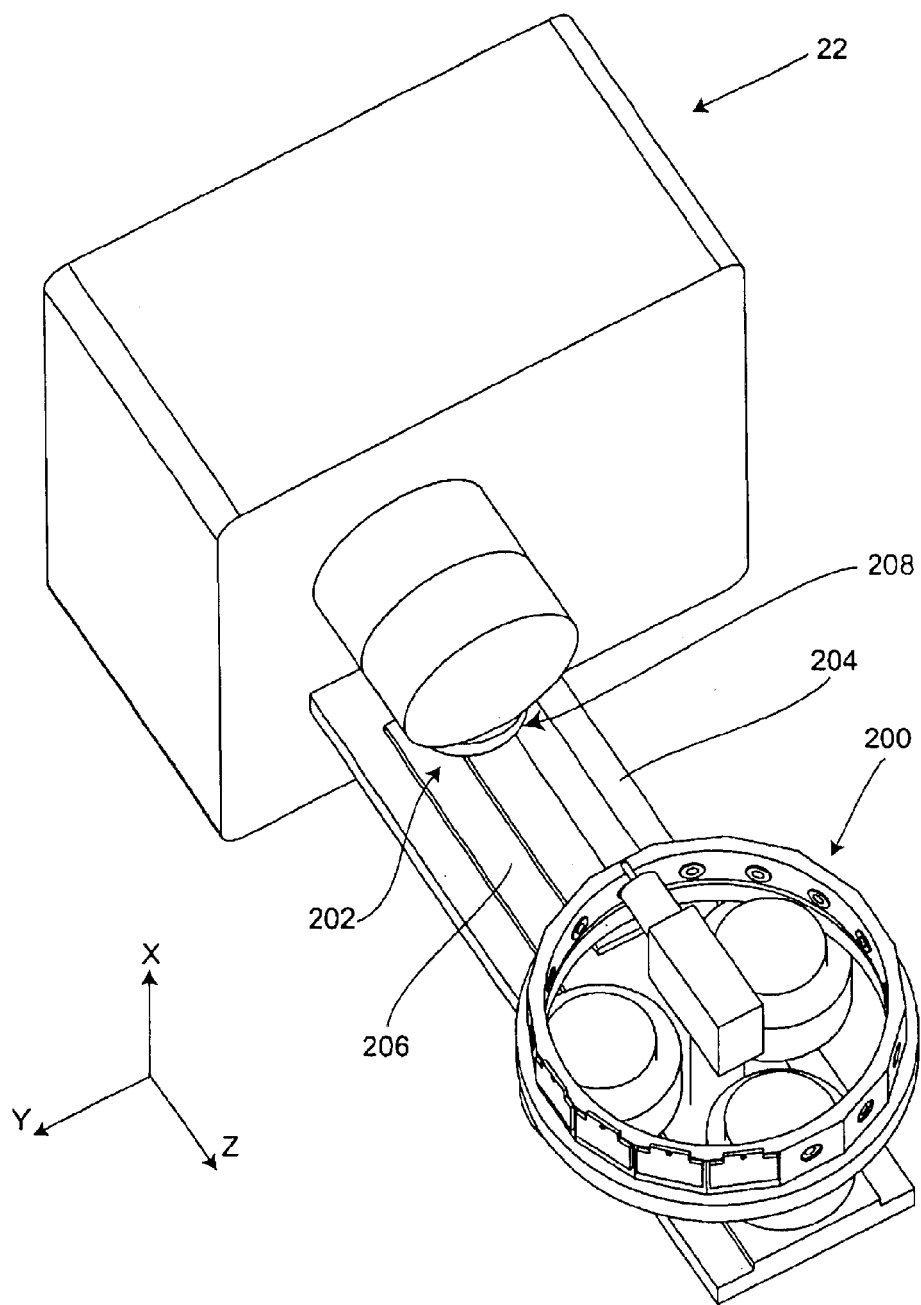
FIG. 10 is a general three-dimensional view of an apparatus made in accordance with a third embodiment of the present invention, wherein a rotary-type sample plate loading/unloading carrier is used.
Figure 11:
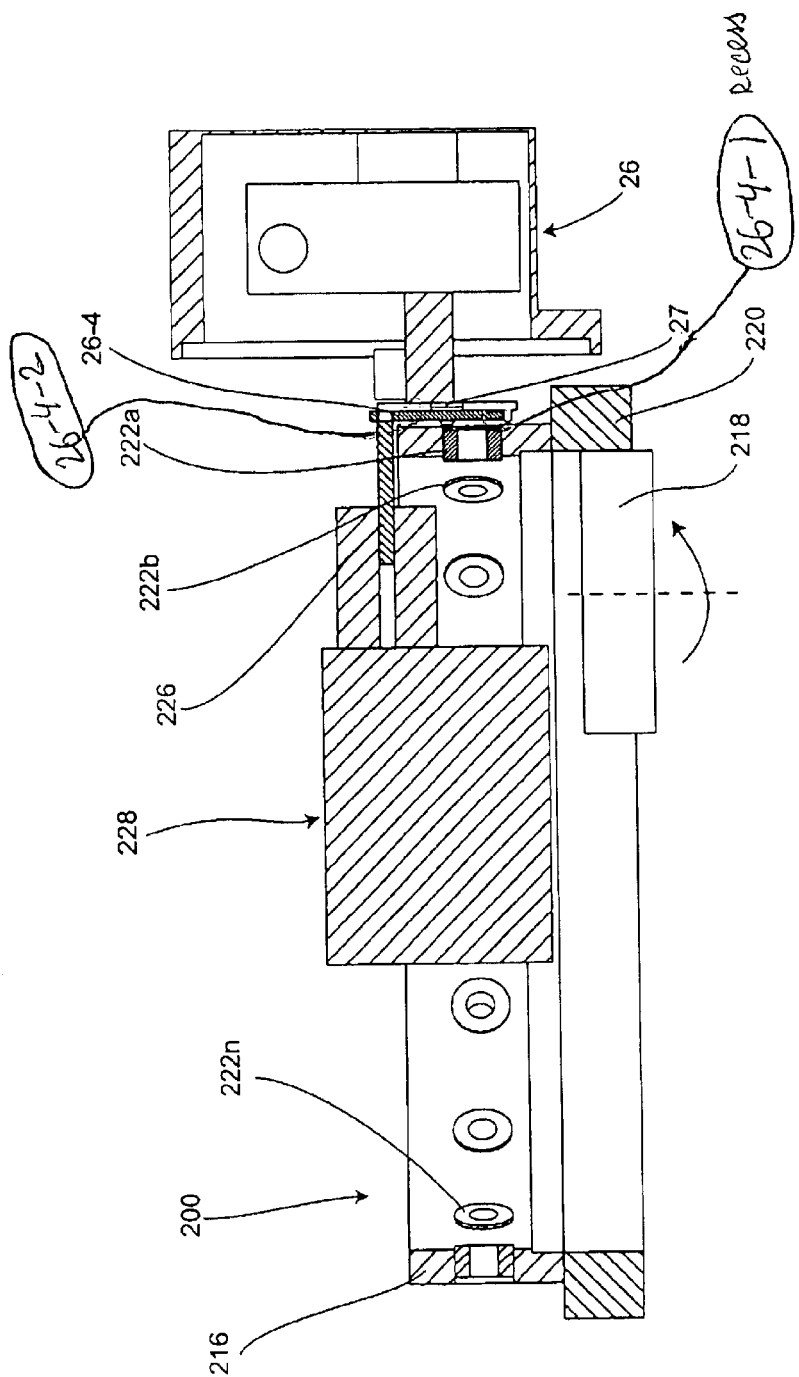
FIG. 11 is a sectional view along lines XI—XI of FIG. 10.
Figure 12:
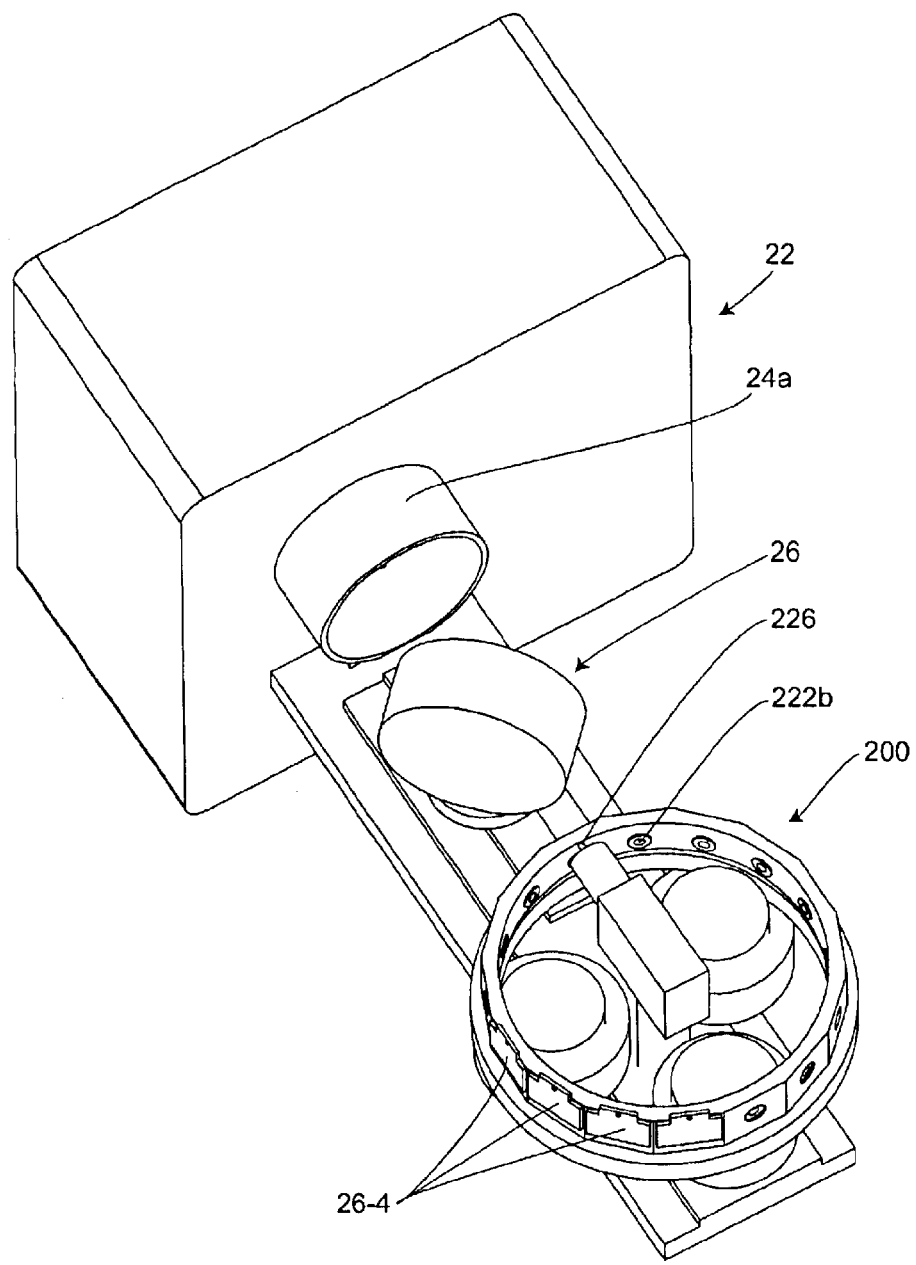
FIG. 12 is a three-dimensional of the apparatus with the rotating carrier.

FIGS. 10 to 12 illustrate the apparatus made in accordance with a third embodiment of the present invention, in which a sample plate carrier comprises a multiple-position rotary-type carrier. Mores specifically, FIG. 10 is a general three-dimensional view of an apparatus of the third embodiment, wherein a rotary-type sample loading/unloading carrier is used.

The apparatus of the third embodiment consists of a mass spectrometer 22, e.g., of the same type as in the previous embodiments, a multiposition sample plate carrier 200 of a rotary type (FIG. 10), and a target flange transportation mechanism 202 for moving the target flange 26 between the position of alignment of the target flange 26 with the center of the orifice (not shown in FIG. 10) of mass spectrometer 22 and the position of alignment with the center of the sample plate in the carrier 200 opposite the mass-spectrometer orifice.

The target flange transportation mechanism 202 consists of guide rails 204 and 206 for guiding a stage 208 that supports the target flange 26 in the Z-axis direction (see Z-axis direction in FIG. 1). For this purpose, the stage 208 has a nut (not shown) that is fixed in the stage 208 and engages a lead screw driven into rotation from a stepper motor (not shown). On the other hand, the target flange 26 is rotatingly supported on the stage 208 and can be rotated around an axis parallel to the X-axis by a stepper motor (not shown).

The construction of the multiposition carrier 200 is shown in FIG. 11, which is a sectional view along lines XI-XI of FIG. 10. The carrier 200 can be loaded with individual sample plates in a remote location and installed on the apparatus as a cartridge. The carrier 200 has a ring-shaped body 216 made from a non-magnetic material and, as shown by the arrow D, can be rotated from a drive motor (not shown in the drawings), e.g., through engagement of a pinion 218 with a tooth ring 220 formed on the periphery of the body 216. The ring-shaped body 216 incorporates a plurality of magnets 222a, 222b . . . 222n inserted into through openings of the body 216 and spaced uniformly spaced from each other at equal distances that linearly correspond to the width slightly exceeding the width of the sample plates 26-4. The outer surface of the ring-shaped body 216 may have shallow recesses 26-4-1 (FIG. 11 having a width equal to the width of the sample plates 26-4 in order to center the plates with the center of the respective magnet 222a, 222b, . . . 222n when the sample plate 26-4, which is made of a material with magnetic properties, is held in its recess 26-4-1 with the working side 26-4-2 of the sample plate 26-4 facing the aforementioned carrier. A pushing rod 226 controlled by a solenoid 228, which, in turn, is controlled from the CPU 82 (FIG. 5) is aligned with the tub 26-4-1-1 (FIG. 2) of the sample plate 26-4. Under a command from the CPU 82, each sample plate 26-4 can be pushed out from the magnet that holds it on the outer surface of the carrier by the pushing rod 226. For returning of the sample plate 26-4 to the sample plate carrier 200, the magnet 222a should be stronger than the magnet 27 of the target flange 26.

The target flange 26 can be placed into the following three positions: 1) the position in which the target flange 26 is oriented with its magnet side towards the orifice of the mass spectrometer 22 and in a docked engagement with the orifice inlet port 24a (FIG. 10); 2) the intermediate position in which the target flange 26 is moved away from the orifice inlet port 24a at a distance sufficient for its rotation by 180° around X-axis (FIG. 12) for facing with its magnet 27 (FIG. 11) towards the outer surface of the body 216; and 3) the loading position (FIG. 11), in which the pushing rod 226 pushes the appropriate sample plate 26-4 from magnet 222a (FIG. 11) towards the magnet 27 of the target flange 26. In FIG. 12 the target flange 26 is shown in an intermediate position of its rotation between the rotary carrier 200 and the orifice inlet port 24a.

In operation, under control of the CPU 82 (FIG. 5), the carrier body 216 performs indexed rotations that position the sample plates 26-4 installed in the positioning slots on the outer surface of the body 216 and held by the respective magnets 222a, 222b, . . . 222n coaxially with the center of the orifice 24 (FIG. 1). The target flange 26 receives the sample plate 26-4 from the rotary carrier 200, turns around by 180° towards the orifice 24, is moved towards the mass spectrometer 22, is docked with the orifice, holds the sample plate 26-4 during analysis, is moved away from the mass spectrometer 22, and turns around by 180°. Meanwhile the carrier 200 turns to a position for receiving the analyzed sample plate or remains in the same position for unloading the sample plate to the same cell of the carrier 200, and then the cycle is repeated for the next sample plate.

Thus it has been shown that, in contrast to the known sample plate transportation system disclosed in aforementioned U.S. Reissued Patent 37,485, in which the sample plates are handled directly and in which all the drive, clamping, and transfer mechanisms operate in vacuum and therefore require the use of complicated and expensive sealing devices, the sample plate carrier transportation mechanisms of the present invention handle the sample plate carriers that supports the sample plates and operate under atmospheric pressure and therefore prevent contamination of the samples and may have a simplified and inexpensive construction.

Furthermore, the invention provides an apparatus for automated sample analysis by AP-MALDI mass spectrometry, wherein an atmospheric pressure interface device, which is docked to the orifice inlet port of the mass spectrometer during loading of the sample plates to the mass spectrometer, is also provided with the function of transfer of the sample plates from the storage cassette to the mass spectrometer. The aforementioned apparatus is provided with programmable fully-automated mechanisms for transporting, loading, and unloading the sample plates into and from the atmospheric pressure interface device. The apparatus of the invention has a simple and inexpensive system for handling the sample plate carriers and sample plates.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, the stepper motors can be replaced by servo motors, or any other drive devices. The guiding mechanisms may be different from lead screw and nut mechanisms, the target flange may be square, the T-shaped grippers may be replaced by snapping grippers with additional motions required for taking the sample plate carriers from the cassette or for insertion into the cassette. The release and clamping of the cassette can be carried out with the use of devices different from the quick-release clamps shown in the drawings, the storage cassette can be placed in a different location than the one shown in the drawings, the sample plate carriers can be extracted from the cassette, by pushing out instead of pulling out, and the sample plates themselves may have a variety of different configurations. Mutually-perpendicular axes X and Y and the plane X-Y formed by these axes, and hence the entire system of modules 42 and 44, can be turned into any angular position around Z-axis without violation the principle of the present invention. Strip-like carriers of the second embodiment and multiposition rotating carrier of the third embodiment may have orientations and constructions different from those shown and described in the specification and drawings. For example, the carrier may be oriented for rotation around the Z-axis, and the sample plates will be arranged in the X-Y plane.

What is claimed is:

1. An apparatus for sample analysis of samples on sample plates by atmospheric pressure matrix assisted laser desorption ionization mass spectrometry comprising:

a mass spectrometer having a vacuum chamber and an ion-sampling orifice for introduction of samples in the form of ionized products of laser desorption of said samples into said vacuum chamber of said mass spectrometer;

at least one sample plate carrier that accommodates at least one sample plate with at least one sample, said at least one sample being held in said sample plate carrier in a position unexposed to the surrounding atmosphere for protecting said at least one sample from contamination when said sample plate is installed in said sample plate carrier for handling and transportation of said sample plate with said at least one sample in the atmospheric pressure environment;

an ionization chamber that comprises a stationary part on said mass spectrometer and a combined moveable gripper and sample plate handling unit disconnectable and moveable away from said mass spectrometer for transportation of said sample plate and having means for taking and releasing said at least one sample plate from said sample plate carrier, means for docked interface with said ion-sampling orifice, and means for holding said at least one sample plate during introduction of said ionized products of laser desorption of said samples into said mass spectrometer.

2. The apparatus of claim 1, further comprising:

a plurality of said sample plate carriers;

a plurality of said sample plates, each one of said sample plate carriers accommodating one of said sample plates; and a sample plate carrier storage means, wherein:

said sample plate carrier storage means has a loading position from which said sample plates are loaded into said combined gripper and sample plate handling unit;

said combined gripper and sample plate handling unit having a working position in which said ionized products of laser desorption of said samples are introduced into said mass spectrometer;

said apparatus further comprising a first module for moving said a combined gripper and sample plate handling unit between said loading position and said working position.

3. The apparatus of claim 1, wherein said sampling orifice has a center and a longitudinal axis passing through said center and defined as Z-axis;

said first module comprising: a first Z-axis drive mechanism that supports said combined gripper and sample plate handling unit and means for moving said combined gripper and sample plate handling unit in the direction parallel to said Z-axis; and first Y-axis drive mechanism that supports said Z-axis drive mechanism and has means for moving said first Z-axis drive mechanism in a direction parallel to a Y-axis that is perpendicular to said Z-axis;

said at least one sample plate carrier comprising a guide channel for guiding said sample plates that are stacked one onto the other.

4. The apparatus of claim 3, wherein said sample plate carrier further comprises a first stopper and a second stopper both insertable into said guide channel and operating in an alternating order so that said first stopper is moved away from said guide channel and releases one sample plate, which is located in said guide channel above said loading position, while said second stopper stops a second sample plate located in said guide channel above said one sample plate, said second sample plate being fed to said loading position by gravity.

5. The apparatus of claim 4, wherein said combined sample plate handling unit comprises:

gripping means for taking said sample plate from said loading position, for transporting said sample plates in said direction parallel to said Y-axis from said loading position to said working position, and for holding said sample plates in said combined sample plate handling unit during said introduction of samples into said mass spectrometer through said ion-sampling orifice;

an X-drive mechanism moveable in the direction parallel to an X-axis that is perpendicular to a plane formed by said Y-axis and Z-axis; and a second Y-drive mechanism moveable in the direction parallel to said Y-axis.

6. The apparatus of claim 5, wherein said gripping means comprises: at least one alignment member and wherein said sample plate carrier has at least one alignment opening for engagement with said at least alignment member; and an electromagnet, which can be energized for attracting said sample plates and de-energized for releasing said sample plates.

7. The apparatus of claim 6, further provided with a control system that comprises a central processing units loaded with input data for controlling motions and sequence of motions performed by said combined gripper and sample plate handling unit, said X-drive mechanism, said first Y-drive mechanism, said second Y-drive mechanism, said Z-drive mechanism, and said electromagnet.

8. The apparatus of claim 1, further provided with a control system that comprises a central processing units loaded with input data for controlling motions and sequence of motions performed by said combined gripper and sample plate handling unit.

9. An apparatus for analysis of samples on sample plates by atmospheric pressure matrix assisted laser desorption ionization mass spectrometry comprising:

a mass spectrometer having a vacuum chamber and an ion-sampling orifice for introduction of samples in the form of ionized products of laser desorption of said samples into said vacuum chamber of said mass spectrometer;

at least one sample plate carrier that accommodates at least one sample plate with at least one sample, said sample plate carrier having a working side that faces said at least one sample for protecting said at least one sample from contamination when said sample plate is installed in said sample plate carrier for handling and transportation of said sample plate with said at least one sample in the substantially atmospheric environment;

an ionization chamber that comprises: a combined moveable gripper and sample plate handling unit disconnectable and moveable away from said mass spectrometer for transportation of said at least one sample plate; means for taking and releasing said at least one sample plate from said sample plate carrier; means for docked interface with said ion-sampling orifice, and means for holding said at least one sample plate during introduction of said ionized products of laser desorption of said samples into said mass spectrometer; said sampling orifice having a center and a longitudinal axis passing through said center and defined as Z-axis;

said apparatus further comprising a first module that comprises:

a first Z-axis drive mechanism heaving means for moving in a direction of an axis parallel to said Z-axis;

a rotating stand rotatingly supported by said first Z-axis drive mechanism, said rotating stand rigidly supporting said combined gripper and sample plate handling unit and having means for rotation together with said combined gripper and sample plate handling unit around an X-axis that is perpendicular to said Z-axis.

10. The apparatus of claim 9, wherein said at least one sample plate carrier comprising means for rotation around an axis parallel to said X-axis and having an outer periphery with a plurality of cells for positioning a plurality of said sample plates, so that during rotation of said sample plate carrier said cells are positioned one by one in alignment with said loading position.

11. The apparatus of claim 10, wherein said combined sample plate handling unit comprises:

gripping means for taking said sample plates from said loading position, for transporting said sample plates in said direction parallel to said Z-axis from said loading position to said working position, and for holding said sample plates in said combined sample plate handling unit during said introduction of said samples into said mass spectrometer through said ion-sampling orifice;

an X-drive mechanism moveable in the direction parallel to said X-axis; and a Y-drive mechanism moveable in the direction parallel to a Y-axis perpendicular to a plane formed by said X-axis and Z-axis.

12. The apparatus of claim 11, wherein said gripping means is an electromagnet; said sample plate carrier further comprising sample plate holding means in each of said cells and a pushing mechanism for pushing said sample plates from said cells in said loading position towards said electromagnet when said combined sample plate handling unit is aligned with said loading position.

13. The apparatus of claim 12, wherein said holding means is a magnet and said pushing means is a pushing rod aligned with said cells and a solenoid driving said pushing rod.

14. The apparatus of claim 13, further comprising a central processing unit which contains input data that controls operation of said gripping means, said X-drive mechanism, said Y-drive mechanism, said Z-drive mechanism, said pushing means, said rotating stand, and said solenoid.

15. The apparatus of claim 14, further provided with a control system that comprises a central processing units loaded with input data for controlling motions and sequence of motions performed by said sample plate carrier handling mechanism for extracting said sample plate carriers from said sample storage means and for transferring them to said stand-by position and by said combined gripper and sample plate handling unit.

16. An apparatus for sample analysis of samples on sample plates by atmospheric pressure matrix assisted laser desorption ionization mass spectrometry comprising:

a mass spectrometer having a vacuum chamber and an ion-sampling orifice for introduction of samples in the form of ionized products of laser desorption of said samples into said vacuum chamber of said mass spectrometer;

at least one sample plate carrier that accommodates at least one sample plate with at least one sample, said sample plate carrier having a working side that faces said at least one sample for protecting said at least one sample from contamination when said sample plate is installed in said sample plate carrier for handling and transportation of said sample plate with said at least one sample in the atmospheric pressure environment an ionization chamber that comprises: a combined moveable gripper and sample plate handling unit disconnectable and moveable away from said mass spectrometer for transportation of said sample plate; means for taking and releasing said at least one sample plate from said sample plate carrier; means for docked interface with said ion-sampling orifice; and means for holding said at least one sample plate during introduction of said ionized products of laser desorption of said samples into said mass spectrometer;

wherein said sampling orifice has a center and a longitudinal axis passing through said center and defined as Z-axis;

said first module comprising: a first Z-axis drive mechanism that supports a first X-axis drive mechanism and has means for moving said first X-axis drive mechanism in a direction parallel to said Z-axis; said first X-drive mechanism having first X-direction means and means for moving said first X-direction means in the direction parallel to an X-axis which is perpendicular to said Z-axis;

said apparatus further comprising a second module having second Z-direction means moveable in the direction parallel to said Z-axis and first Y-direction means moveable in the direction of Y-axis, which is perpendicular to said X-axis;

said combined sample plate handling unit being rigidly supported by said Y-direction means.

17. The apparatus of claim 16, further comprising sample storage means and a sample plate carrier handling mechanism comprising first gripping means on said first X-direction means for extracting said sample plate carriers from said sample storage means.

18. The apparatus of claim 17, wherein said combined sample plate handling unit comprises:

second gripping means for taking said sample plates from said stand-by position, for transporting said sample plates in said direction parallel to said Y-axis from said stand-by position to said center of said ion-sampling orifice, and for holding said sample plates in said combined sample plate handling unit during said introduction of samples into said mass spectrometer through said ion-sampling orifice;

second X-direction means moveable in the direction parallel to said X-axis; and second Y-direction means moveable in the direction parallel to said Y-axis.

19. The apparatus of claim 18, wherein each of said sample plate carriers is provided with means for releasable engagement with said first gripping means so that said first gripping means can engage said means for releasable engagement and extract said sample plate carrier from said sample storage means.

20. The apparatus of claim 19, wherein said means for releasable engagement comprise at least one slot having a profiled configuration and wherein said first gripping means comprise at least one projection having a configuration conforming to said profiles configuration made so that said at least one projection can be introduced into and released from said slot by moving said first gripper only in said direction parallel to said Z-axis.

21. The apparatus of claim 17, wherein said second gripping means is an electromagnet, which can be energized for gripping said sample plates and de-energized for releasing said sample plates.

22. The apparatus of claim 21, wherein each of said sample plate carriers is provided with means for releasable engagement with said first gripping means so that said first gripping means can engage said means for releasable engagement and extract said sample plate carrier from said sample storage means.

23. The apparatus of claim 22, wherein said means for releasable engagement comprise at least one slot having a profiled configuration and wherein said first gripping means comprise at least one projection having a configuration conforming to said profiles configuration made so that said at least one projection can be introduced into and released from said slot by moving said first gripper only in said direction parallel to said Z-axis.

24. The apparatus of claim 16, wherein each of said sample plate carriers is provided with means for releasable engagement with said first gripping means so that said first gripping means can engage said means for releasable engagement and extract said sample plate carrier from said sample storage means.

25. The apparatus of claim 24, wherein said means for releasable engagement comprise at least one slot having a profiled configuration and wherein said first gripping means comprise at least one projection having a configuration conforming to said profiles configuration made so that said at least one projection can be introduced into and released from said slot by moving said first gripper only in said direction parallel to said Z-axis.

26. The apparatus of claim 16, wherein each of said sample plate carriers is a sample plate carrier that supports a sample plate with a plurality of sample cells arranged in a predetermined order, said sample storage means comprising a cassette with a plurality of slots for supporting a plurality of said sample plate carriers, said cassette extending in said direction parallel to Z-axis and said sample plate carriers being arranged in said slots in a Y-X plane formed by said X-axis and said Y-axis.

27. An apparatus for sample analysis of samples on sample plates by atmospheric pressure matrix assisted laser desorption ionization mass spectrometry comprising:

a mass spectrometer having a vacuum chamber and an ion-sampling orifice for introduction of samples in the form of ionized products of laser desorption of said samples into said vacuum chamber of said mass spectrometer;

at least one sample plate carrier that accommodates at least one sample plate with at least one sample;

a combined moveable gripper and sample plate handling unit disconnectable from said mass spectrometer and having means for taking and releasing said at least one sample plate, means for docked interface with said ion-sampling orifice, and means for holding said at least one sample plate during introduction of said ionized products of laser desorption of said samples into said mass spectrometer; said sampling orifice having a center and a longitudinal axis passing through said center and defined as Z-axis;

said first module comprising: a first Z-axis drive mechanism that supports a first X-axis drive mechanism and has means for moving said first X-axis drive mechanism in a direction parallel to said Z-axis; said first X-drive mechanism having first X-direction means and means for moving said first X-direction means in the direction parallel to an X-axis which is perpendicular to said Z-axis;

said apparatus further comprising a second module having second Z-direction means moveable in the direction parallel to said Z-axis and first Y-direction means moveable in the direction of Y-axis, which is perpendicular to said X-axis;

said combined sample plate handling unit being rigidly supported by said Y-direction means;

each of said sample plate carriers being a sample plate carrier that supports a sample plate with a plurality of sample cells arranged in a predetermined order, said sample storage means comprising a cassette with a plurality of slots for supporting a plurality of said sample plate carriers, said cassette extending in said direction parallel to Z-axis and said sample plate carriers being arranged in said slots in a Y-X plane formed by said X-axis and said Y-axis; and, said first Z-direction means comprising a first stationary stage with a first lead screw arranged in said direction parallel to said Z-axis, a first drive motor for rotating said first lead screw and a first nut rigidly connected to said first X-direction means; said first X-direction means comprising a second stage installed on first X-direction means and having a second lead screw arranged in said direction parallel to said X-axis and a second nut rigidly connected to said second stage.

28. The apparatus of claim 27, wherein said second stage has first gripping means for extracting said sample plate carriers from said sample storage means, each of said sample plate carriers being provided with means for releasable engagement with said first gripping means so that said first gripping means can engage said means for releasable engagement and extract said sample plate carrier from said sample storage means.

29. The apparatus of claim 28, wherein said means for releasable engagement comprise at least one slot having a profiled configuration and wherein said first gripping means comprise at least one projection having a configuration conforming to said profiles configuration made so that said at least one projection can be introduced into and released from said slot by moving said first gripper only in said direction parallel to said Z-axis.

30. The apparatus of claim 29, wherein said combined sample plate handling unit comprises:

second gripping means for taking said sample plates from said stand-by position, for transporting said sample plates in said direction parallel to said Y-axis from said stand-by position to said center of said ion-sampling orifice, and for holding said sample plates in said combined sample plate handling unit during said introduction of samples into said mass spectrometer through said ion-sampling orifice;

second X-direction means moveable in the direction parallel to said X-axis; and second Y-direction means moveable in the direction parallel to said Y-axis.

31. The apparatus of claim 30, wherein said second gripping means is an electromagnet, which can be energized for gripping said sample plates and de-energized for releasing said sample plates.

32. The apparatus of claim 27, wherein said second Z-direction means comprises a second stationary stage with a third lead screw arranged in said direction parallel to said Z-axis, a third drive motor for rotating said third lead screw and a third nut rigidly connected to said first Y-direction means; said first Y-direction means comprising a third stage installed on said second Z-direction means and having a fourth lead screw arranged in said direction parallel to said Y-axis and a fourth nut rigidly connected to said third stage.

33. The apparatus of claim 32, said third stage rigidly supports said combined sample plate handling unit that comprises:
second gripping means for taking said sample plates from said stand-by position, for transporting said sample plates in said direction parallel to said Y-axis from said stand-by position to said center of said ion-sampling orifice, and for holding said sample plates in said combined sample plate handling unit during said introduction of samples into said mass spectrometer through said ion-sampling orifice;

second X-direction means moveable in the direction parallel to said X-axis; and second Y-direction means moveable in the direction parallel to said Y-axis.

34. The apparatus of claim 33, wherein said second gripping means is an electromagnet, which can be energized for gripping said sample plates and de-energized for releasing said sample plates.

35. The apparatus of claim 27, further provided with a control system that comprises a central processing units loaded with input data for controlling motions and sequence of motions performed by said sample plate carrier handling mechanism for extracting said sample plates from said sample storage means and for transferring them to said stand-by position and by said combined gripper and sample plate handling unit.

36. A method for sample analysis of samples on sample plates by atmospheric pressure ionization matrix assisted laser desorption ionization mass spectrometry comprising the steps of:

providing at least one sample plate carrier for carrying at least one of said sample plates with at least one sample in the atmospheric pressure environment;

providing a mass spectrometer having a vacuum chamber and an ion-sampling orifice for introduction of samples in the form of ionized products of laser desorption of said samples on sample plates into said vacuum chamber of said mass spectrometer;

providing sample carrier storage means for storing said at least one sample plate carrier with said at least one sample plate;

providing a combined gripper and sample plate handling unit; and using said combined gripper and sample plate handling unit for loading/unloading said sample plates into and from said at least one sample plate carrier and for docked interface with said ion-sampling orifice and for holding said sample plates during introduction of said ionized products of laser desorption of said samples into said mass spectrometer;

while being in said at least one sample plate carrier, said at least one sample is maintained in a position protected from contact with said atmospheric pressure environment, in said protected position said at least one sample facing said sample plate carrier.

37. The method of claim 36, further comprising the step of inserting said at least one of said sample plates into said at least one sample plate carrier prior to loading into said sample carrier storage means.

38. The method of claim 37, said step of inserting is carried out in a location remote from said mass spectrometer.

39. The method of claim 37, wherein said sample plate carriers are used in a plurality and wherein each of said sample plate carriers carries one of said sample plates.

* * * * *